(12) United States Patent
Cormode et al.

(10) Patent No.: US 10,940,217 B2
(45) Date of Patent: Mar. 9, 2021

(54) POLYPHOSPHAZENE DELIVERY SYSTEM FOR INORGANIC NANOCRYSTALS

(71) Applicants: THE TRUSTEES OF THE UNIVERSITY OF PENNSYLVANIA, Philadelphia, PA (US); THE PENN STATE RESEARCH FOUNDATION, University Park, PA (US)

(72) Inventors: David Peter Cormode, Philadelphia, PA (US); Peter Chhour, Wayne, PA (US); Andrew Tsourkas, Bryn Mawr, PA (US); Harry Allcock, State College, PA (US); Rabe'e Cheheltani, Philadelphia, PA (US)

(73) Assignees: The Trustees Of The University Of Pennsylvania, Philadelphia, PA (US); The Penn State Research Foundation, University Park, PA (US)

(*) Notice: Subject to any disclaimer, the term of this patent is extended or adjusted under 35 U.S.C. 154(b) by 0 days.

(21) Appl. No.: 15/126,103

(22) PCT Filed: Mar. 18, 2015

(86) PCT No.: PCT/US2015/021198
§ 371 (c)(1),
(2) Date: Sep. 14, 2016

(87) PCT Pub. No.: WO2015/143010
PCT Pub. Date: Sep. 24, 2015

(65) Prior Publication Data
US 2017/0000910 A1 Jan. 5, 2017

Related U.S. Application Data

(60) Provisional application No. 61/954,791, filed on Mar. 18, 2014.

(51) Int. Cl.
| | | |
|---|---|---|
| A61K 49/18 | (2006.01) | |
| A61K 49/00 | (2006.01) | |
| A61K 9/51 | (2006.01) | |
| A61K 49/04 | (2006.01) | |
| A61B 18/04 | (2006.01) | |
| A61B 18/18 | (2006.01) | |
| A61K 9/107 | (2006.01) | |
| A61K 38/38 | (2006.01) | |
| A61K 41/00 | (2020.01) | |
| A61N 5/10 | (2006.01) | |
| A61B 18/00 | (2006.01) | |

(52) U.S. Cl.
CPC .......... *A61K 49/1809* (2013.01); *A61B 18/04* (2013.01); *A61B 18/18* (2013.01); *A61K 9/1075* (2013.01); *A61K 9/5146* (2013.01); *A61K 38/385* (2013.01); *A61K 41/0023* (2013.01); *A61K 41/0038* (2013.01); *A61K 49/0067* (2013.01); *A61K 49/0082* (2013.01); *A61K 49/0428* (2013.01); *A61K 49/0466* (2013.01); *A61K 49/1857* (2013.01); *A61N 5/10* (2013.01); *A61B 2018/00577* (2013.01); *A61N 2005/1098* (2013.01)

(58) Field of Classification Search
None
See application file for complete search history.

(56) References Cited

U.S. PATENT DOCUMENTS

| | | |
|---|---|---|
| 6,645,444 B2 | 11/2003 | Goldstein |
| 9,138,491 B2 | 9/2015 | Sung et al. |
| 2004/0247624 A1 | 12/2004 | Unger |

FOREIGN PATENT DOCUMENTS

| | | |
|---|---|---|
| KR | 20090000859 A | 1/2009 |
| WO | 2008121077 A1 | 10/2008 |
| WO | 2012009448 A2 | 1/2012 |
| WO | 2012030134 A2 | 3/2012 |
| WO | 2012121528 A2 | 9/2012 |
| WO | 2012137999 A1 | 10/2012 |

OTHER PUBLICATIONS

Hu et al (Facile Synthesis of Superparamagnetic Fe3O4@polyphosphazene@Au Shells for Magnetic Resonance Imaging and Photothermal Therapy. ACS Appl. Mater. Interfaces, 2013, 5 (11), pp. 4586-4591; herein after "HU1").*
Zhang et al (Bioorg Med Chem. Aug. 2010; 18(15):5528-34.).*
Hu et al (Highly Cross-Linked and Biocompatible Polyphosphazene-Coated Superparamagnetic Fe3O4 Nanoparticles for Magnetic Resonance Imaging. Langmuir, 2013, 29 (29), pp. 9156-9163; herein after "HU2").*
Andrianov et al (Polyphosphazene Microspheres: Preparation by Ionic Complexation of Phosphazene Polyacids with Spermine. Applied Polymer Science, vol. 101, 414-419 (2006)).*
Jokerst et al (Nanoparticle PEGylation for imaging and therapy. Nanomedicine (Lond). Jun. 2011 ; 6(4): 715-728) (Year: 2011).*

(Continued)

*Primary Examiner* — Jake M Vu

(74) *Attorney, Agent, or Firm* — Saul Ewing Arnstein & Lehr LLP; Kathryn Doyle; Brian R. Landry

(57) ABSTRACT

Nanoclusters comprising inorganic nanocrystals and a biodegradable polymer are disclosed. The inorganic nanocrystals have a mean particle size of 1 to 500 nm. The inorganic nanocrystals are contained within a core of the nanoclusters, on the surface of the nanoclusters, contained within a core of the nanoclusters, dispersed throughout the nanoclusters, or a combination thereof. The biodegradable polymer allows the inorganic nanocrystals to be excreted renally over a period of time. The nanoclusters can be used for medical imaging or other biomedical applications.

9 Claims, 23 Drawing Sheets

(56) References Cited

OTHER PUBLICATIONS

Arvizo et al (Gold nanoparticles: Opportunities and Challenges in Nanomedicine. Expert Opin Drug Deliv. Jun. 2010 ; 7(6): 753-763). (Year: 2010).*

Teasdale et al (Polyphosphazenes: Multifunctional, Biodegradable Vehicles for Drug and Gene Delivery. Polymers (Basel). Mar. 1, 2013; 5(1): 161-187) (Year: 2013).*

Allijn et al., "Gold Nanocrystals Labeling Allows Low-Density Lipoprotein Imaging form the Subcellular to Macroscopic Level", ACS Nano, Nov. 26, 2013, vol. 7, No. 1, 19 pages.

Link et al., "Alloy Formation of Gold-Silver Nanoparticles and the Dependence of the Plasmon Absorption on Their Composition", J. Phys. Chem. B., 1999, vol. 103 No. 18, pp. 3529-3533.

Simpson et al.,"Unexpected Toxicity of Monolayer protected Gold Clusters Eliminated by PEG-Thoil Place Exchange Reactions", Chem. Res. Toxicil., Oct. 18, 2101, vol. 23 No. 10, pp. 1608-1616.

Brust et al., "Synthesis of thoil-derivatised gold nanoparticles in a two-phase liquid-liquid system", 1994, Chem. Commum., pp. 801-802.

International Search Report and Written Opinion for International Application No. PCT/US2015/021198, dated Aug. 5, 2015, 9 pages.

International Preliminary Report on Patentability for International Application No. PCT/US2015/021198, dated Sep. 20, 2016, 7 pages. 2016.

Hu et al., "Facile Synthesis of Superparamagnetic FE304@Polyphosphazene@AU Shells for Magnetic Resonance Imaging and Photothermal Therapy," American Chemical Society 4586 DX.DOI.ORG/10.121/AM400843D: ACS Appl. Mater Interfaces (2013) 5, p. 4586-4591, www.acsami.org.

Almeida et al., "In Vivo Biodistribution of Nanoparticles," Nanomedicine (2011) BO., 6. No. 5, pp. 815-835, DOI 10.224/NNM 11.79 (DOI: 10.2217 /NM 11.79), Abstract.

Turkevich, J., Stevenson, P. C., and Hillier, J. (1951) "A Study of the Nucleation and Growth Processes in the Synthesis of Colloidal Gold," Discuss. Faraday Soc. 11, 55-75.

Extended European Search Report for European Application No. 15765306.4, dated Nov. 24, 2017, 9 pages.

Communication pursuant to Article 94(3) EPC, European Patent Application No. 15 765 306.4, dated Sep. 16, 2019.

\* cited by examiner

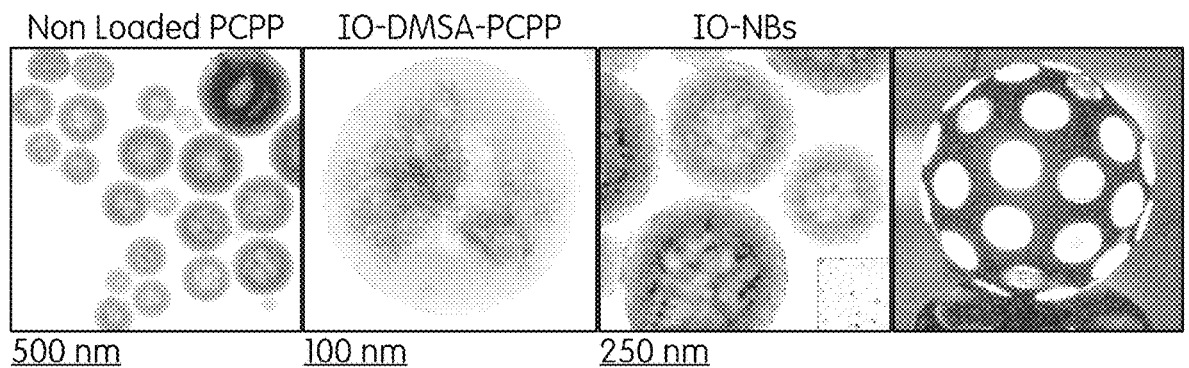
| Non Loaded PCPP | IO-DMSA-PCPP | IO-NBs | |
|---|---|---|---|
| 500 nm | 100 nm | 250 nm | |
| FIG. 5a | FIG. 5b | FIG. 5c | FIG. 5d |
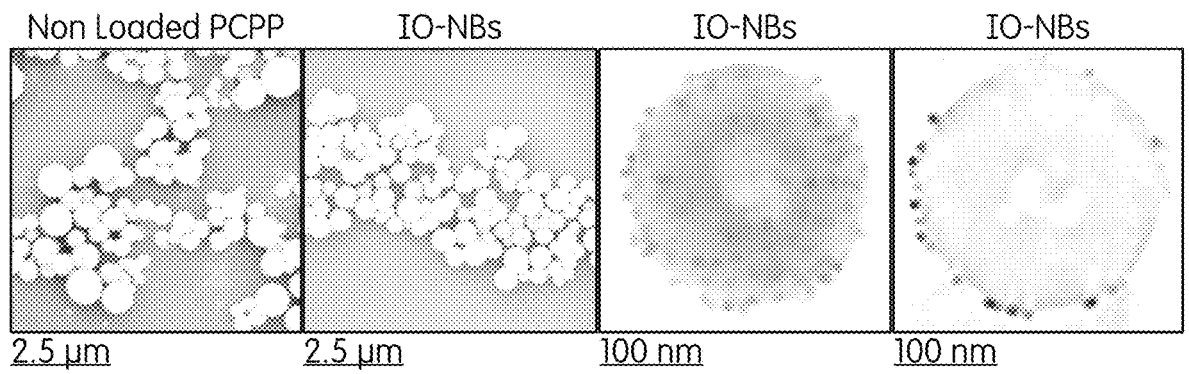
| Non Loaded PCPP | IO-NBs | IO-NBs | IO-NBs |
|---|---|---|---|
| 2.5 μm | 2.5 μm | 100 nm | 100 nm |
| FIG. 5e | FIG. 5f | FIG. 5g | FIG. 5h |

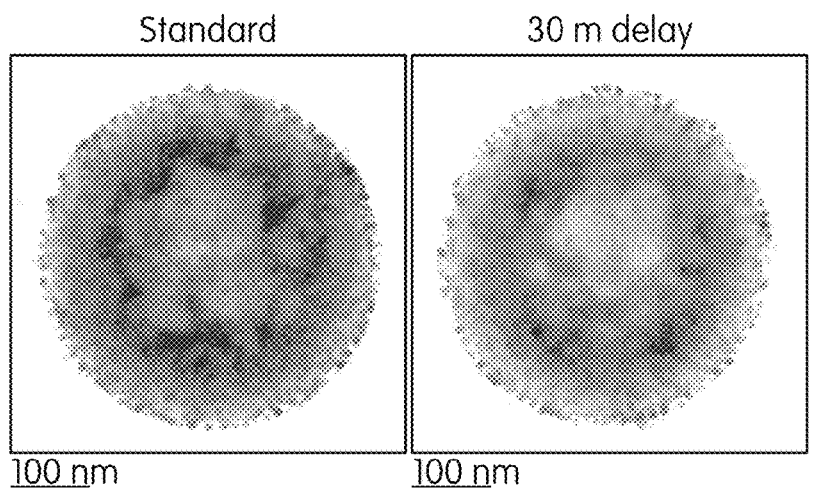
FIG. 6a  Standard
FIG. 6b  30 m delay
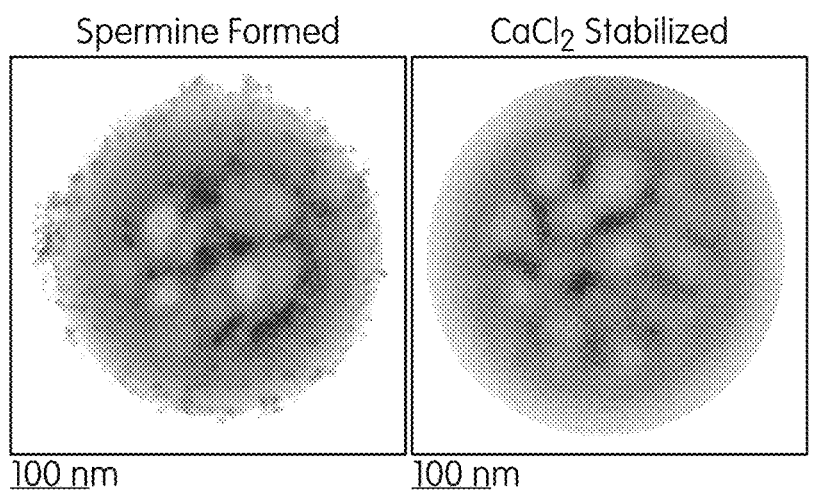
FIG. 6c  Spermine Formed
FIG. 6d  CaCl$_2$ Stabilized
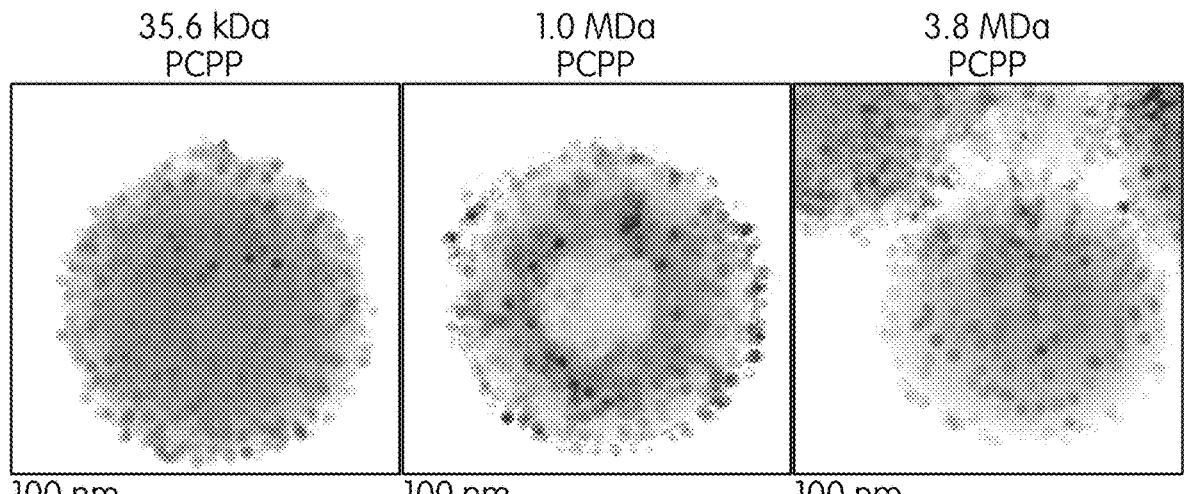
FIG. 7a  35.6 kDa PCPP
FIG. 7b  1.0 MDa PCPP
FIG. 7c  3.8 MDa PCPP

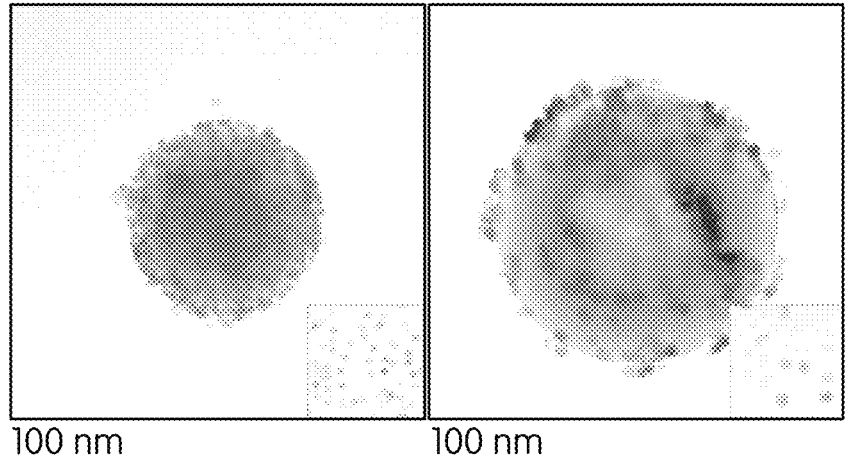
FIG. 10a  GdF₄ Spheres PCPP
FIG. 10b  GdF₄ Rods PCPP
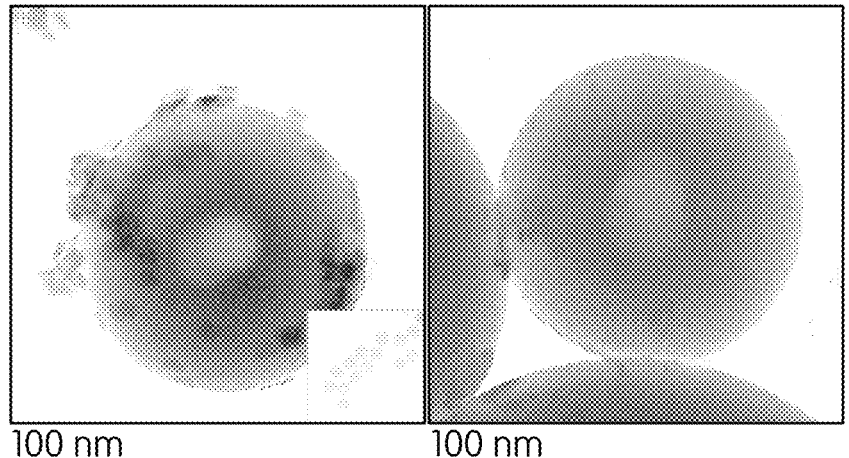
FIG. 10c  LaF₃ Discs PCPP
FIG. 10d  CdS QDs PCPP Sub-5 nm gold nanoparticles | Biodegradable polyphophazene | Gold nanoparticles encapsulated in polymer matrix | Polymer degradation in vivo leads to gold nanoparticle release for excretion

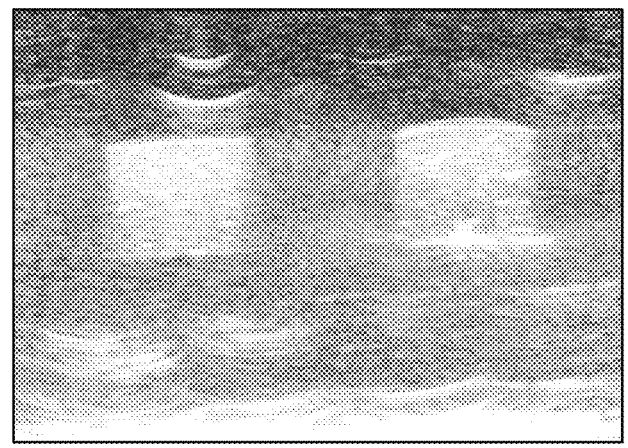
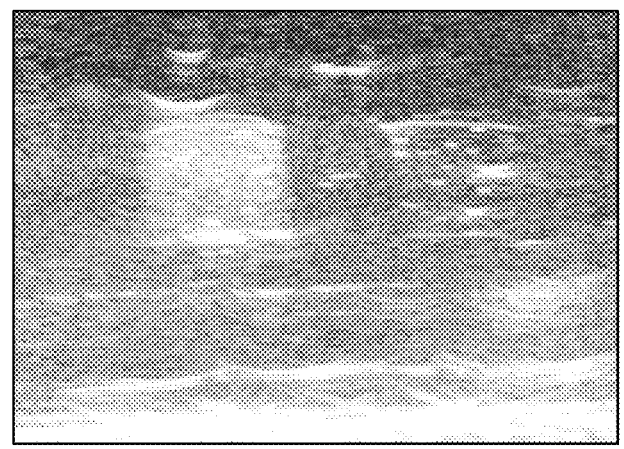
FIG. 23

POLYPHOSPHAZENE DELIVERY SYSTEM FOR INORGANIC NANOCRYSTALS

CROSS REFERENCE TO RELATED APPLICATIONS

This application is the U.S. National Phase application of PCT International Application PCT/US2015/021198, filed on Mar. 18, 2015, which claims the benefit of U.S. Provisional Application No. 61/954,791, titled "POLYPHOSPHAZENE DELIVERY SYSTEM FOR INORGANIC NANOCRYSTALS", filed on Mar. 18, 2014, the entirety of which are incorporated by reference herein.

STATEMENT REGARDING FEDERALLY-SPONSORED RESEARCH

This invention was made with government support under grant numbers EB012165, RR024134, and EB013754 awarded by the National Institutes of Health. The government has certain rights in the invention.

FIELD OF THE INVENTION

The present invention relates to polymer delivery systems for contrast agents, imaging agents and/or drugs comprising polymer encapsulated diagnostically active nanocrystals and/or drugs.

BACKGROUND OF THE INVENTION

Imaging agents and contrast agents find widespread uses in diagnostic techniques. X-ray based imaging techniques, such as radiography, computed tomography (CT), mammography, dual energy mammography, tomosynthesis or fluoroscopy, are widely used in medical diagnosis and interventional radiology.

CT is a whole body imaging technique. It is cheap, simple to use and very fast (image acquisition time <10s). The speed of modern CT scanners has been permitted by the advent of multi-slice scanning, with models possessing as many as 320 slices currently available. This allows several centimeters of tissue to be imaged in one scanner rotation. In combination with gating to compensate for heart motion, scanners with as few as 64 slices can acquire high resolution images of the coronary arteries in less than 5s, while the patient holds his/her breath. CT has become a workhorse of cardiovascular imaging and is highly useful for identifying occlusions in coronary arteries, allowing diagnosis of coronary artery disease. Fluoroscopy is a real-time imaging X-ray based technique commonly used in interventional radiology for stent emplacement, lymphangiography and other techniques. The primary form of contrast agent for X-ray based imaging is iodinated small molecules such as iopamidol or iodixanol. These agents are used in approximately 50% of CT scans, or 34 million cases in 2007 in the USA. The majority of cardiovascular CT studies are performed with iodine contrast. The concentration of these agents achieved in the kidneys is approximately 100 times that in plasma and about 30% of the concentration of the solution in the bottle. It is thought that the presence of such concentrations of agent in the kidney can cause acute kidney injury, especially in patients who will experience such concentrations of agent for lengthy periods due to low glomerular filtration rates.

It is clear that there has been a very marked increase in the number of patients with renal insufficiency in the USA over the past 30 years. The percentage of people aged over 60 with chronic kidney disease increased from 18.8% to 26% between studies performed from 1988-1994 to 2001-2008. Furthermore, the prevalence of end stage renal failure increased from 290 to 1,738 per million of the population from 1980 to 2009. Guidelines have been issued worldwide that patients with renal insufficiency should not be given iodinated contrast agents due to the risk of causing kidney failure, i.e. contrast-induced nephropathy. The increase in the incidence of type 2 diabetes in patients is thought to be a major reason for this increase, as renal insufficiency is a common consequence of type 2 diabetes. The number of Americans with diabetes of either type is predicted to increase from 10% currently to 20-30% by 2050 by the Centers for Disease Control and Prevention. Patients with type 2 diabetes are also at increased risk of cardiovascular disease. Therefore, there will be an increasing population for whom iodinated contrast agents are contraindicated, but will be at high risk of having a cardiovascular event, which would require contrast enhanced CT imaging or fluoroscopy in order to locate occlusions and emplace stents. New X-ray contrast agents that are less nephrotoxic are in great need for use with this growing patient population.

Novel contrast agents for fluoroscopy could potentially have great value in a range of interventional radiology procedures such as stent emplacement.

Nanoparticles made of heavy elements such as iodine, gold, bismuth, or platinum attenuate X-rays strongly. Such nanoparticles may produce stronger contrast than iodinated agents, may be designed to circulate longer than iodinated contrast agents, may be detected with spectral CT or dual energy CT, and may be highly biocompatible.

It has been shown that nanoparticles larger than 5 nm will be retained within the body, potentially for years, whereas nanoparticles smaller than 5 nm can be swiftly excreted via the kidneys and the urine. Unfortunately, some of the critical strengths of nanoparticles, i.e. long circulation times and accumulation in diseased tissues, arise due to their large size (>5 nm) preventing swift urinary excretion of nanoparticles. In CT/fluoroscopy, long circulating nanoparticles would be advantageous for a number of applications such as vascular imaging. They would also simplify imaging protocols, as the agent could be injected intravenously before the scan, as opposed to iodinated small molecules, which require catheter placement and triggered imaging as contrast is injected—if the timing of the scan is off, the vascular contrast is poor. The long-term retention of large nanoparticles would be a concern that would likely prevent their eventual clinical application. Additional, such long-term retention could also interfere with subsequent imaging studies.

Smaller nanoparticles (i.e., particles smaller than 5 nm) have their own associated shortcomings. Small nanoparticles are excreted quickly (excretion half-life on the order of minutes, e.g., 5 minutes or less) and must be administered in large quantities and/or multiple uptake events for high loading. The high loading may also place a greater burden on the kidneys to excrete the nanoparticles in a short period of time. Due to the short excretion half-life, the time window available to image the patient is very limited. Small nanoparticles also have a higher surface area, which may heighten the chance of adverse effects on biocompatibility.

Despite the extensive literature on gold nanoparticles, there has been very little work done on small gold nanoparticles that are easily excreted. The vast majority of the work that has been done with gold nanoparticles for biomedical applications has used structures too large to be excreted via the urine. Overall, in the nanomedicine field there are only a few examples of easily excreted metal nanoparticles.

Thus, there is a need for nanoparticles that can be excreted, e.g., pass the kidneys and be swiftly excreted via the urine. In addition, to avoid renal damage it may be beneficial for the injected contrast agent dose to be filtered via the kidney gradually, as opposed to over a few minutes.

Nanoparticles, including metal and inorganic nanocrystals, are also of interest in other diagnostic techniques, such as, for example, magnetic resonance imaging (MRI), photoacoustic imaging, surface-enhanced Raman spectroscopy, fluorescence imaging and other techniques.

Imaging agents and contrast agents are also useful for identifying targeted drug delivery. Using imaging agents or contrast agents with existing diagnostic techniques may allow for confirmation that a drug has been delivered to a desired location. Furthermore, the nanocrystals may have use in enhancing the therapeutic effects of radiochemistry, photothermal ablations, or other treatments.

Incorporation of inorganic nanocrystals into polymeric particles is a topic of great interest. Such assemblies have a wide range of applications including uses in catalysis, energy, drug delivery, and medical imaging. Often the structural organization of a particle will dictate the function and behavior of the nanoparticles in a given application. Therefore, the ability to control localization of nanocrystals via self-assembly would be a valuable tool in the synthesis of nanocrystal/polymer composite particles.

Many studies incorporating inorganic nanocrystals into polymers have used nanocrystals modified to be hydrophobic. Breakdown of these nanoparticles in vivo would result in release of the hydrophobically coated nanocrystals, which would then immediately precipitate or be opsonized and not be excreted. Therefore, there is a need for delivery systems for hydrophilic nanocrystals that can be excreted.

The present inventors have discovered nanoclusters comprising hydrophilic inorganic nanocrystals and/or drugs loaded into a polymer matrix that may address one or more of the shortcomings identified above.

SUMMARY OF THE INVENTION

The present invention relates to nanoclusters comprising inorganic nanocrystals and/or drugs and a biocompatible and biodegradable polymer, wherein the inorganic nanocrystals may be renally excreted.

A first aspect of the present invention relates to a nanocluster comprising:
 a plurality of inorganic nanocrystals;
 a biodegradable polymer;
 wherein the plurality of inorganic nanocrystals are contained on a surface of or within the biodegradable polymer.

A second aspect of the present invention relates to a method comprising:
 administering to a patient a plurality of nanoclusters each comprising a plurality of inorganic nanocrystals; and
 imaging the patient with x-ray imaging, computed tomography (CT), magnetic resonance imaging (MRI), photoacoustic imaging, fluorescence, fluoroscopy or other imaging techniques.

Another aspect of the present invention relates to targeted drug delivery comprising:
 administering to a patient a plurality of nanoclusters, wherein the nanoclusters comprise a plurality of inorganic nanocrystals and at least one drug or wherein the plurality of nanoclusters comprise nanoclusters comprising a plurality of inorganic nanocrystals and nanoclusters comprising at least one drug; and
 imaging the patient with x-ray imaging, computed tomography (CT), magnetic resonance imaging (MRI), photoacoustic imaging, fluorescence, fluoroscopy or other imaging techniques.

BRIEF DESCRIPTION OF THE DRAWINGS

FIG. 5 shows electron microscopy images of PCPP nanospheres.

FIG. 6 shows TEM images of nanoclusters resulting from synthesis variations.

FIG. 7 shows electron microscopy images of PCPP nanospheres using different molecular weight PCPP.

FIG. 10 shows electron microscopy images of PCPP nanosphere surfaces loaded with different nanocrystals.

FIG. 23 demonstrates the contrast produced by nanoclusters loaded with gold in photoacoustic imaging.

DETAILED DESCRIPTION OF THE INVENTION

Figure 1A:
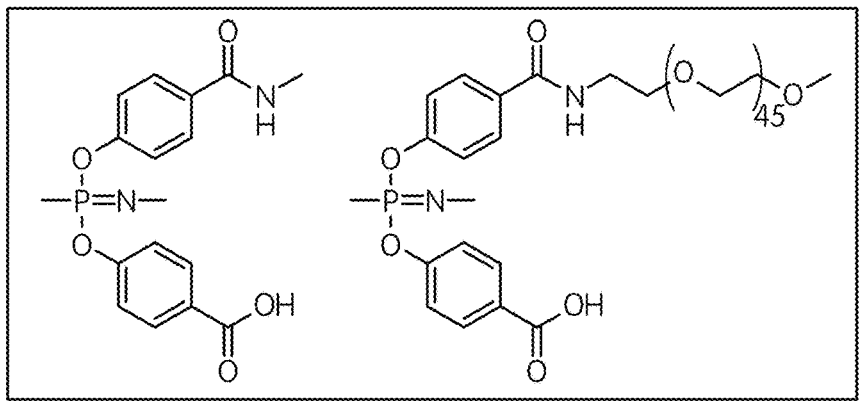
FIG. 1 shows PEG-modified polymers, cross-linkers, and carboxylic acids.

One aspect of the present disclosure relates to nanoclusters comprising inorganic nanocrystals and a biocompatible and biodegradable polymer, wherein the inorganic nanocrystals may be renally excreted.

As used herein, the term "nanoclusters" refers to a nanoscale grouping of inorganic nanocrystals on or within a polymer. The nanocrystals may be contained on the surface of the nanocluster, contained within the core of the nanocluster (i.e., concentrated within the interior of the nanocluster), dispersed throughout the nanocluster, or a combination thereof.

According to at least one embodiment, the nanocluster may also comprise a drug. Alternatively, the nanoclusters may comprise at least two different types of nanoclusters. In at least one embodiment, the nanoclusters may comprise a first type of nanocluster comprising inorganic nanocrystals and a second type of nanocluster comprising a drug.

As used herein, the term "nanocrystal" refers to an inorganic nanoscale particle. Examples of nanocrystals include metal particles (such as gold, tantalum, lanthanum, ytterbium, bismuth, platinum, silver, etc.), alloys of metals (e.g. gold and silver, gold and copper, copper and silver and others), combinations of metals (e.g. part one metal and part another metal, such as gold-silver core-shell structures), inorganic compounds, such as, for example, iron oxide, nanophosphors (e.g., gadolinium fluoride), quantum dots (e.g., cadmium selenide or zinc sulfide), silica and other compounds or salts, as well as combined metal-compound nanoparticles such as a silver core coated with silica or a silica core coated with gold and other structures known to those familiar with the art.

As used herein, the term "drug" is used to broadly describe chemical compounds that have a biological effect on humans or other animals. For example, a drug may comprise biopharmaceuticals (i.e., biologics) or pharmaceuticals and includes peptides, antibodies, proteins, nucleic acids, synthesized and natural chemical compounds, etc.

According to at least one embodiment, the nanoclusters comprise nanocrystals having a mean particle size of 500 nm or less, such as, for example, 250 nm or less, 100 nm or less, 50 nm or less, 25 nm or less, 15 nm or less, 10 nm or less, or 5 nm or less. In at least one embodiment, the nanocrystals have a mean particle size of 4 nm or less, 3 nm or less, 2 nm or less, or 1 nm or less. Smaller nanocrystals may also be used. In other embodiments, the nanocrystals can be larger and can range in size from 1 to 500 nm.

The nanocrystals may have an approximately spherical shape, a rod shape, a disc shape, or any other morphology.

The nanocrystal may comprise any diagnostically active material. As used herein, the term "diagnostically active" means a material that may be detected by a diagnostic instrument, such as, for example, a CT imaging system or an MRI scanner. The nanocrystal may be a contrast agent or an imaging agent.

According to at least one embodiment, the nanocrystals are chosen from compounds suitable for use as contrast agents in an X-ray based diagnostic technique (e.g., CT imaging or fluoroscopy), such as, iodine, gold, silver, bismuth, yttrium, ytterbium, tantalum, tungsten, or platinum, as well as alloys, combinations, and salts thereof. In at least one embodiment, the nanocrystals are chosen from gold and bismuth.

Figure 24A:
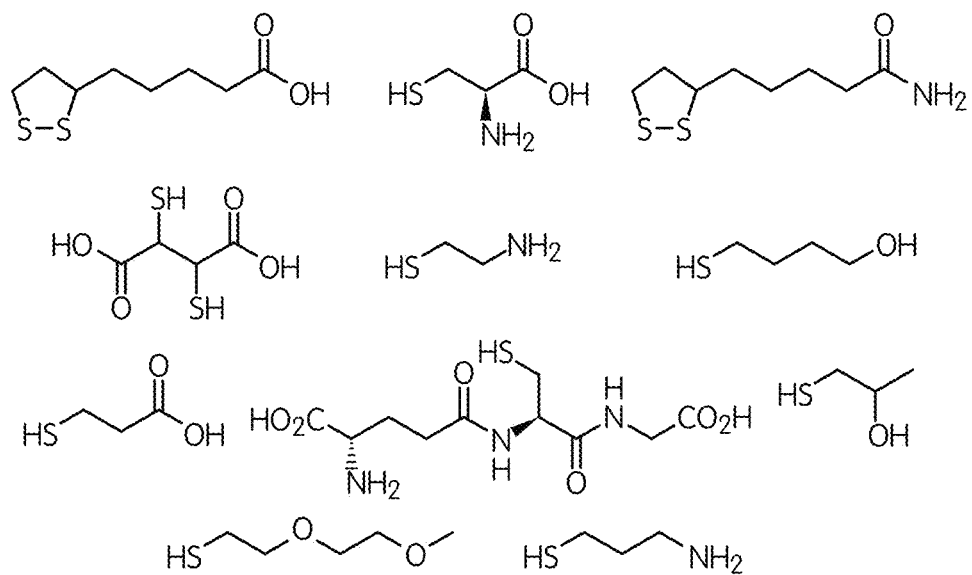
FIG. 24 shows (a) the chemical structures of small gold-silver alloy nanoparticle (GSAN) coating ligands; (b) and (c) show TEM images of gold-silver alloy nanoparticles of 90% silver and 80% silver alloys, respectively; (d) shows a photo of 100%, 80%, 90%, and 50% silver gold-silver alloy nanoparticles; (e) shows a UV/visible spectra of gold-silver alloy nanoparticles; and (f) shows the effect of gold concentration on the viability of cells incubated with gold-silver alloy nanoparticle formulations.
Figures 24B, 24C:
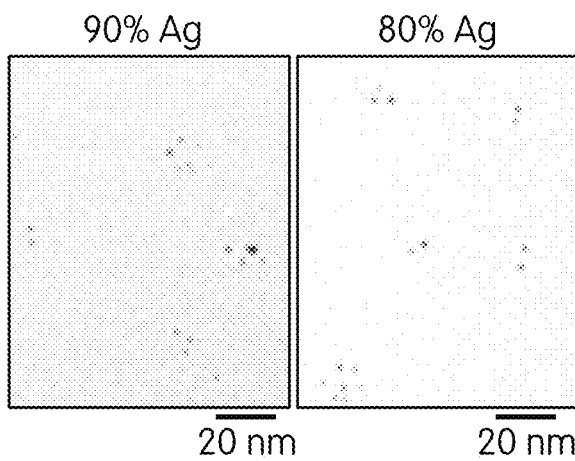
Figure 24D:
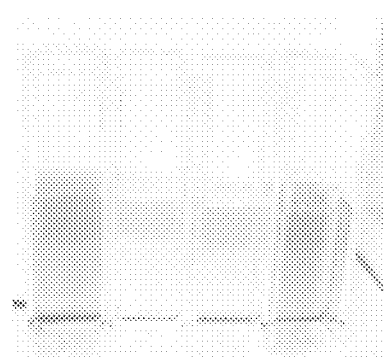
Figure 24E:
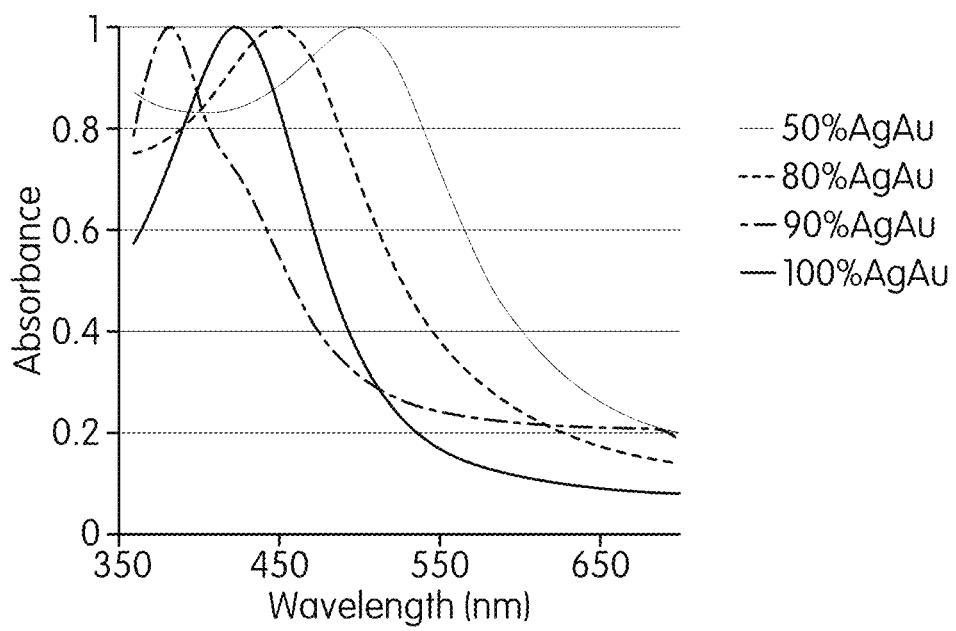
Figure 24F:
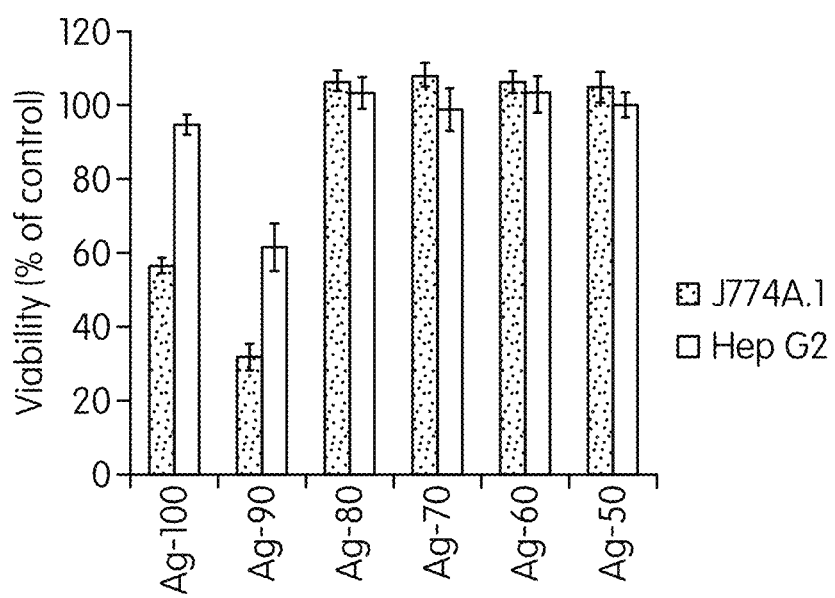

In accordance with at least one embodiment, the nanocrystals are chosen from alloys of metals, such as, for example, gold and silver, gold and copper, or copper and silver. Alloying two different metals may allow for tuning of the properties of the nanocrystals compared to using the individual metals themselves. For example, alloying gold with silver may improve the biocompatibility of silver nanocrystals by changing the electrochemical potential of nanocrystals. As shown in FIG. 24F, alloying gold with silver to create gold-silver alloy nanoparticles (GSAN) can improve the biocompatibility of the nanocrystals. For example, when GSAN nanocrystals comprise 80% silver and 20% gold, the viability of cells incubated with the GSAN improves significantly compared to GSAN nanocrystals comprising 90% silver and 10% gold. The inventors have also surprisingly found that gold does not attenuate the signal of silver when used in dual energy (DE) mammography.

According to at least one embodiment, the nanocrystals comprise a combination of two or more metals. For example, the nanocrystals may comprise a core-shell particle comprising a core of one metal coated with a shell of a second metal. In at least one embodiment, the shell may be continuous or discontinuous. For example, the nanocrystal may comprise a silver core coated with a gold shell. The gold shell may completely cover the silver core, or the gold shell may have openings through which the underlying silver core is exposed.

In at least one embodiment, the nanocrystals comprise a compound suitable for use as an MRI imaging agent, such as, for example, iron oxide. The iron oxide may be doped or undoped. For example, the iron oxide may be doped with manganese, cobalt, nickel, or bismuth. The dopant may be selected, for example, to increase or decrease the contrast of the image.

According to at least one embodiment, the nanocrystal is chosen from nanophosphors. Nanophosphors include, but are not limited to, gadolinium nanospheres (e.g., gadolinium fluoride) and lanthanum nanospheres.

In accordance with at least one embodiment, the nanocrystals are chosen from quantum dots. Examples of quantum dots include, but are not limited to, cadmium selenide and zinc sulfide.

The polymer may be selected from any known biocompatible and biodegradable polymer. In at least one embodiment, the polymer is chosen from polyphosphazenes, such as, for example, poly(bis(4-carboxyphenoxy)phosphazene) (PCPP) and poly(carboxylatophenoxy)(glycinato) polyphosphazenes (PCGPPs). Polyphosphazenes have tunable functionality and biocompatibility. By modifying the polyphosphazene side chains and molecular weight, the biodegradation rate of polymers can be controlled. The polymers may range in molecular weight from 10,000 to 10,000,000, from 30,000 to 3,000,000, from 100,000 to 1,000,000 or others. The polymers may be straight chain, branched or have other conformations. The side groups may be 4-hydroxybenzoic acid, glycine, glutamic acid, other amino acids, methoxyethoxyethoxy, glycerol, imidazole, or others known to those familiar in the art. The polymer may be a co-polymer of two or more types of polymers, such as a polyphosphazene and another type of polymer, e.g. PEG, polyacrylic acid, poly(D,L-lactic-co-glycolic acid), polycaprolactone, poly(vinyl-pyrrolidone), poly(acryl-amide), poly(glycerol) and others known to those familiar with the art. In addition, the polymer could be formed from two or more types of polyphosphazene. The polymeric component could also be composed of multiple different types of polymers or co-polymers mixed together.

The polymer may be cross-linked to further control the biodegradation rate of the polymer, as well as the loading of the nanocrystal. The crosslinker may be selected to react with the functional groups of the polymer. For example, when the polymer comprises a carboxylated polymer such as PCPP, the crosslinker may comprise a diamine or polyamine such as spermine. Other suitable crosslinkers would be known to those of ordinary skill in the art.

Figure 1B:
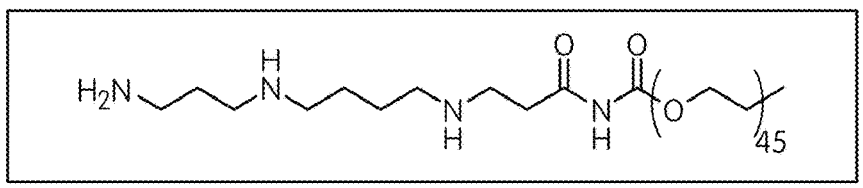
Figure 1C:
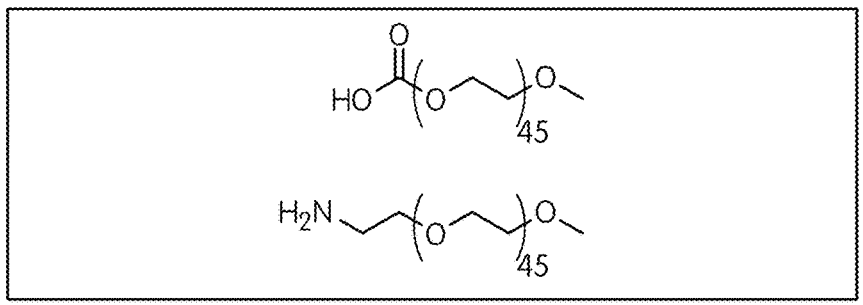
Figure 21:
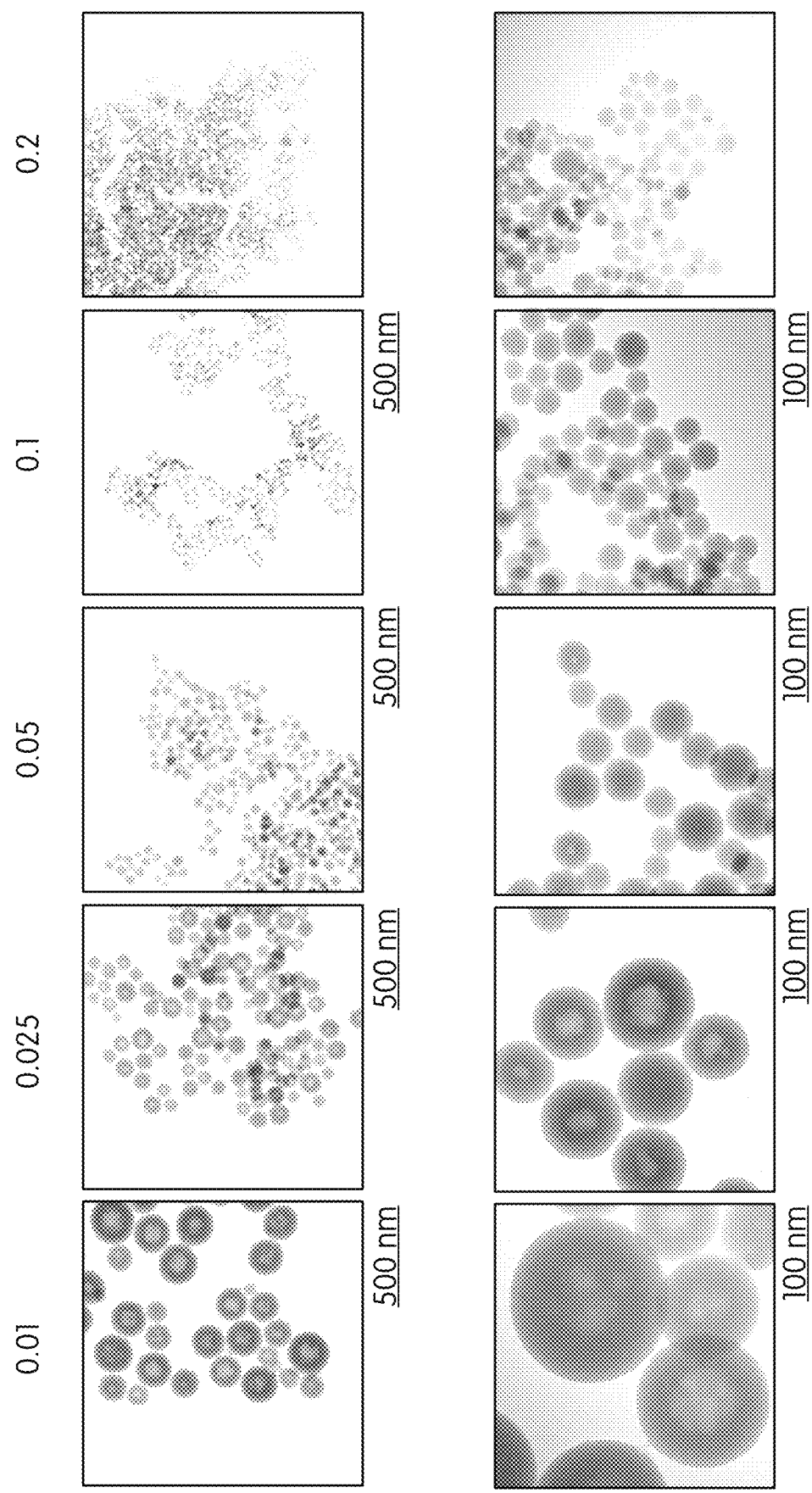
FIG. 21 shows variation of nanocluster size by controlling the amount of PLL-PEG used in the formation of the nanoclusters.

The polymer and/or crosslinker may be further modified. For example, the polymer-nanoparticle system (PCPP-NP) may be coated with polyethylene glycol (PEG) to provide long circulation half-lives and avoid uptake by the reticuloendothelial system. Three possibilities are to chemically modify the polymer, chemically modify the spermine or to add PEG molecules that terminate in acids or amines (FIG. 1). The polymer could be coupled with small amounts of amines such as methylamine or an amino-PEG molecule. Small proportions of the spermine could be modified with acids such as a carboxy-PEG. Last, amino-PEG or carboxy-PEG could be added at various points in the reaction process. The size can be controlled via the concentration of the polymer and by varying the amount of PEG included in the synthetic process. It has also been discovered that including small amounts of polylysine (PLL)-PEG block copolymers to the synthesis may allow long circulation half-lives and avoid uptake by the reticuloendothelial system, as well as allow the control of the nanoparticle size by adjusting the amount of PLL-PEG used. FIG. 21 shows the variation of nanocluster size by adjusting the amount of PLL-PEG from 0.01 mg/ml to 0.2 mg/ml.

Figure 19:
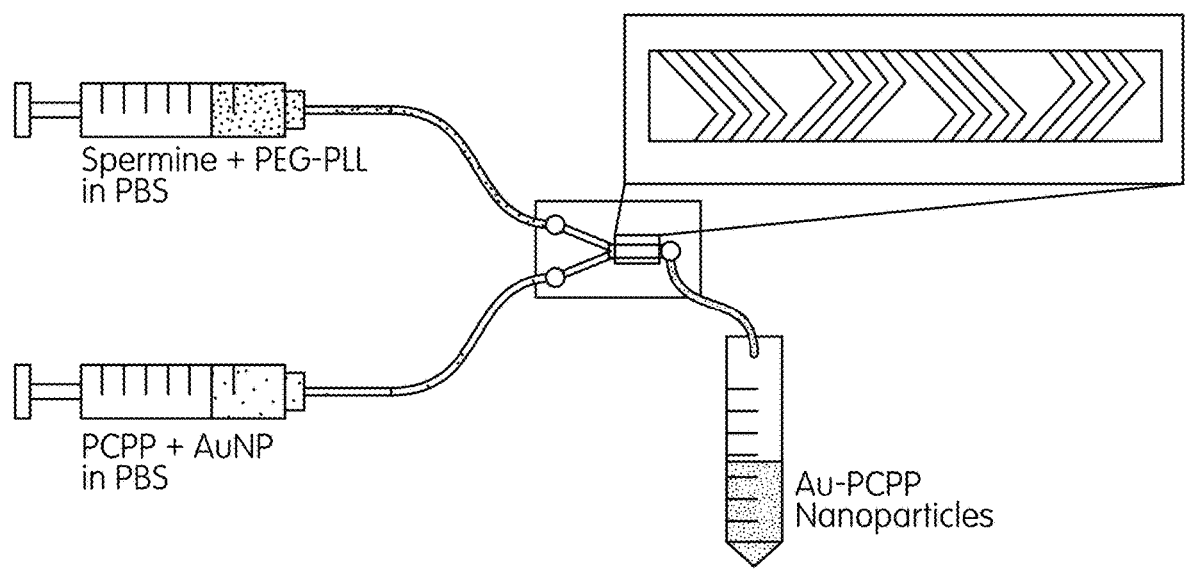
FIG. 19 shows a schematic representation of a microfluidic system that may be used to produce nanoclusters.
Figure 20:
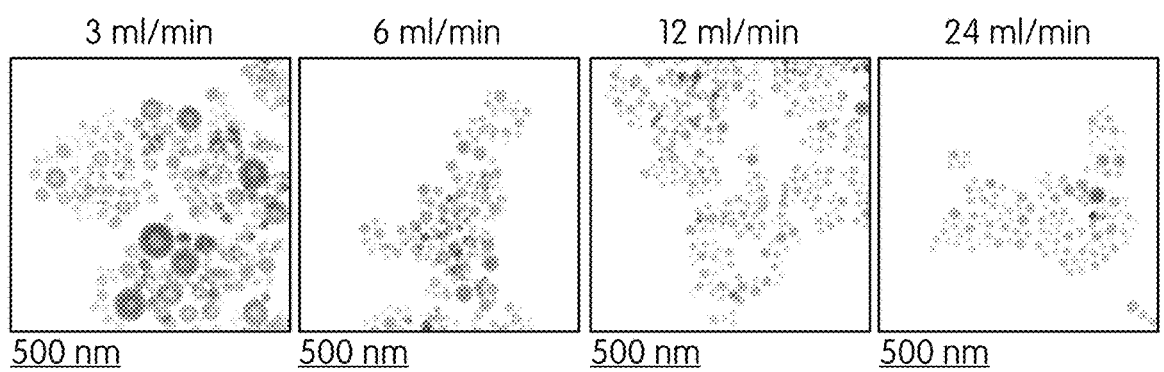
FIG. 20 shows the particle size distribution of nanoclusters produced by modifying the flow rate within a microfluidic device.

In at least one embodiment of the present invention, the nanoclusters can be made using microfluidic devices, which may also allow the size of the nanoclusters to be controlled. FIG. 19 shows one example of a microfluidic device containing a herringbone mixing region that can be used to control the size of the nanoclusters. In at least one embodiment, it is also possible to adjust flow rates within the microfluidic chips to control the size distribution of the nanoclusters. As shown in FIG. 20, higher flow rates may result in greater uniformity of size.

Figure 2:
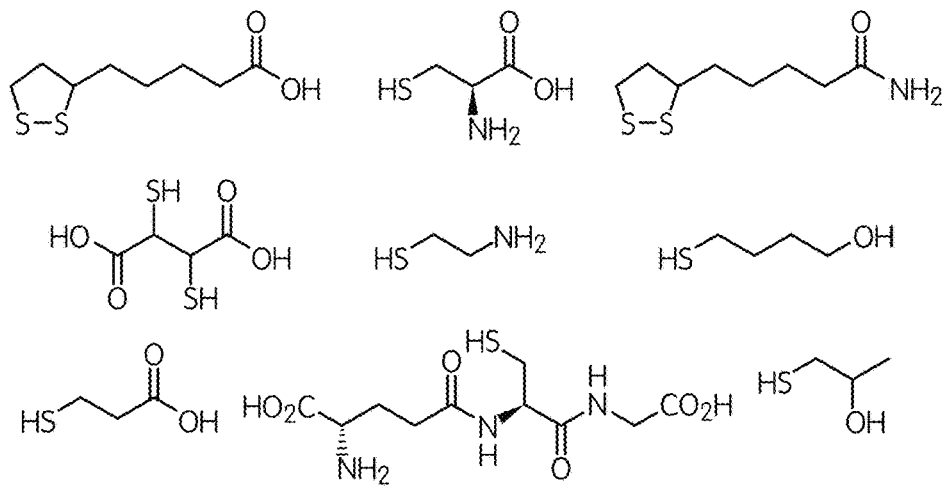
FIG. 2 shows examples of nanocrystal ligands.

The nanocrystals may comprise a ligand such as a coating ligand or capping ligand. The present inventors have surprisingly discovered that the ligand may be used to control the interaction of the nanocrystal with the particle. For example, the ligand may allow the nanocrystal to be loaded on the surface of the polymer, concentrated within the core of the polymer, or dispersed throughout the polymer. Non-limiting examples of ligands that may be used in accordance with the present invention are shown in FIG. 2. Other examples of ligands include glucose and other phospholipids. In at least one embodiment, the ligand is selected from 11-mercaptoundecanoic acid and glutathione.

According to at least one embodiment, the nanoclusters of the present invention may further comprise one or more targeting agents (also known as "targeting ligands"). The targeting agent may be a molecule or a structure that provides targeting of the nanocluster to a desired organ, tissue or cell. Non-limiting examples of such targeting agents include peptides, antibodies, proteins, nucleic acids, small molecules, etc. The targeting agent(s) are preferably attached to the outer surface of the nanocluster for targeted imaging. A nanocluster comprising one or more targeting agents can be targeted to specific diseased areas of the subject's body.

According to at least one embodiment, the nanoclusters may have a mean size ranging about 10 nm to about 750 nm. In at least one embodiment, the nanoclusters may have a mean size less than about 600 nm, less than about 500 nm, less than about 400 nm, less than about 300 nm, less than about 200 nm, less than about 100 nm, or less than about 50 nm. Smaller nanoclusters may also be used.

According to at least one embodiment, the nanoclusters may have an excretion half-life of at least 30 minutes, such as, for example, at least 45 minutes, at least 1 hour, at least 2 hours, at least 4 hours or at least 24 hours.

The nanoclusters disclosed herein may be used in X-ray based diagnostic imaging techniques, such as, for example, CT imaging, mammography, dual energy (DE) mammography, tomosynthesis, MRI scanning, fluorescence imaging, photoacoustic imaging, or other techniques using diagnostically active agents. FIG. 23 shows the contrast produced by gold nanoclusters in photoacoustic imaging. In FIG. 23, the gold-containing nanoclusters (Au-PCPP) show stronger contrast compared to gold nanoparticles (Au-NP) alone.

Figure 3A:
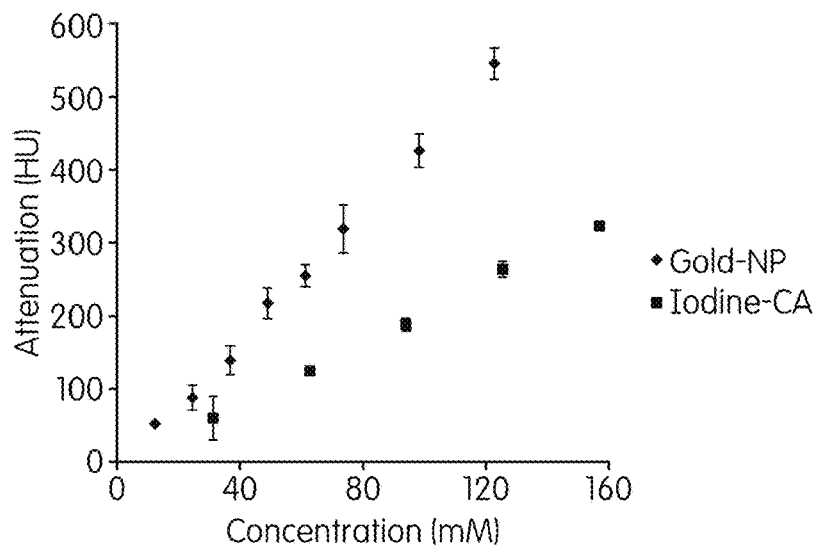
FIG. 3 shows (A) a graph comparing the attenuation of gold to iodine, (B) spectral CT detection of gold nanoparticles, and (C) microCT images of a mouse injected with PEG-coated gold nanoparticles.
Figure 3B:
Figure 3C:
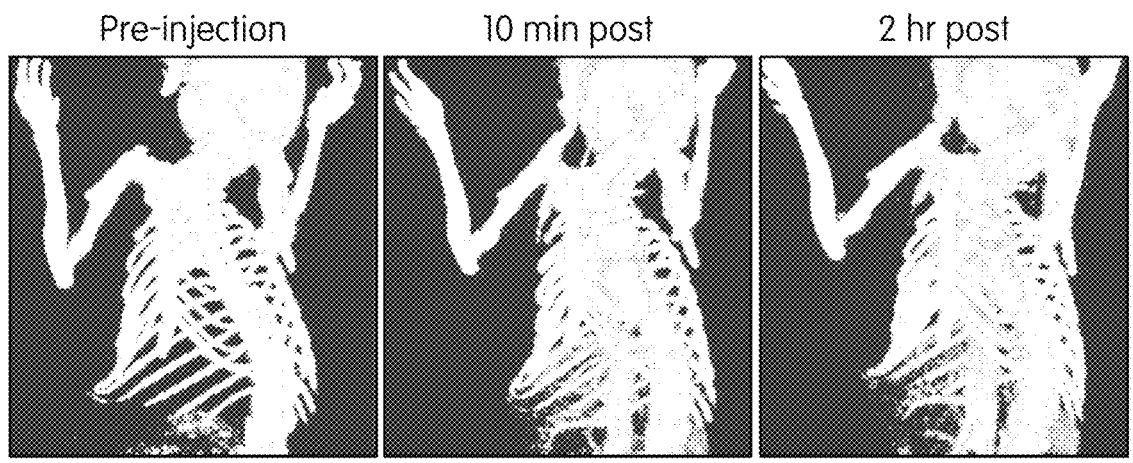
Figure 13A:
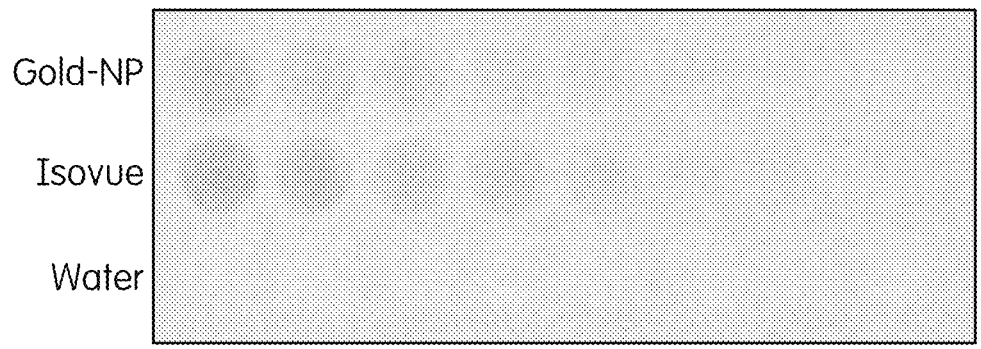
FIG. 13 shows a fluoroscopy image of gold nanoparticles compared to an iodine contrast agent and a graph of the respective signal intensities.
Figure 13B:
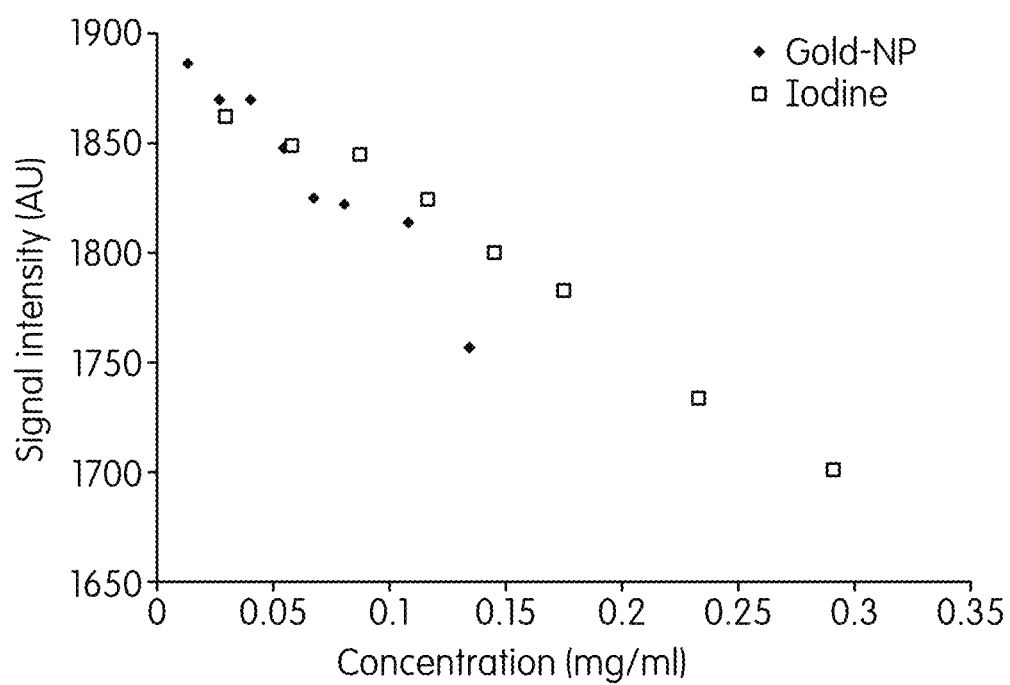

The approved iodinated molecules for use in CT imaging carry between three to six iodine atoms. Gold, on the other hand, is extremely dense (19.7 g/cm$^3$) and a gold nanoparticle with a 3 nm core would contain approximately 850 gold atoms. For an equivalent dose of contrast agent, 150-300 times fewer 3 nm core gold nanoparticles would be injected than iodinated molecules. This should place a lower burden on the kidneys in terms of the number of excretion events needed, so gold nanoparticles may be more compatible with patients with poor kidney function than iodinated agents. Gold produces higher contrast than iodine, can be specifically detected with techniques such as dual and spectral CT, and is regarded as highly biocompatible. Data shows that the attenuation of gold is compared with that of iodine is displayed in FIG. 3A, while spectral CT detection of gold nanoparticles (Au-NP) is shown in FIG. 3B. FIG. 3C shows acquired microCT images of a mouse injected with 15 nm PEG-coated gold nanoparticles, where long lasting vascular contrast is observed. FIG. 13 shows angiography data comparing gold nanoparticles to an iodine contrast agent. Although the examples are based on gold nanoparticles, the experiments disclosed herein on excretion, coatings, encapsulation and so forth, could be applied to other types of metal cores in further work.

According to at least one embodiment, the nanoclusters of long-circulating gold nanoparticles, therefore, would be larger than 5 nm, but would slowly break down into sub-5 nm components that could be excreted via the urinary system. This approach would result in low concentrations of gold nanoparticles reaching the kidneys over an extended time, which would minimize any potential nephrotoxicity. A schematic of the formation of the nanoclusters and their degradation is shown in FIG. 17.

Figure 18A:
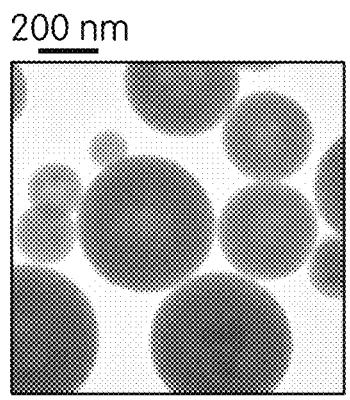
FIG. 18 shows (a) a TEM image of Au-PCPP nanoparticles 6 months after synthesis; (b) Photos of AU-PCPP at different pHs; (c) degradation of Au-PCPP in 10% serum incubated at 37° C.; (d) a TEM image of cells incubated with PCPP-NP; (e) ICP-MS analysis of media over macrophages after incubation with Au-PCPP; and (f) a TEM image of AuGlu after release from PCPP.
Figure 18B:
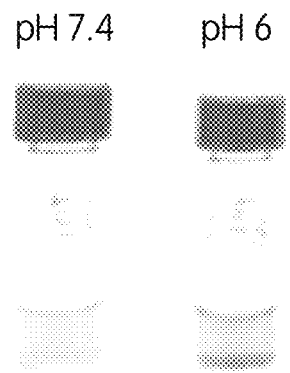
Figure 18C:
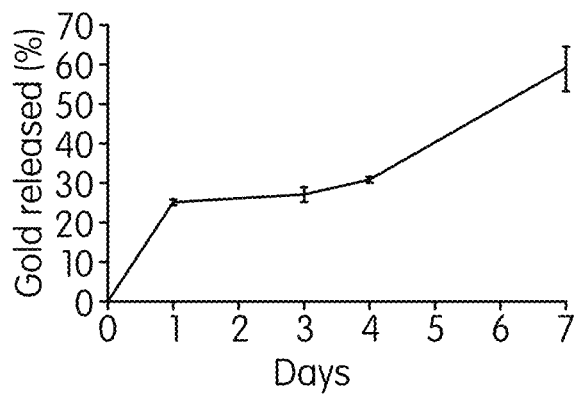
Figure 18D:
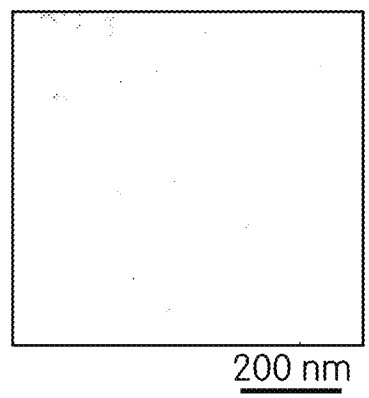
Figure 18E:
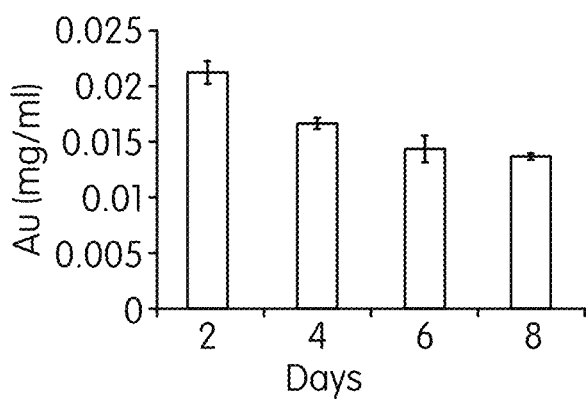
Figure 18F:
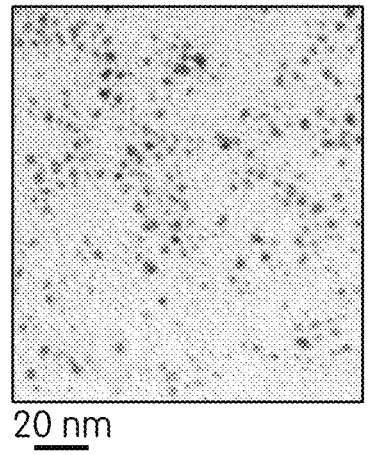

FIG. 18 shows the stability of polyphosphazene polymer nanoclusters comprising gold nanocrystals (Au-PCPP) over time (FIG. 18A), at different pHs (FIG. 18B), upon incubation in serum (FIG. 18C), and upon incubation and release of the gold nanoparticles (Au-NPs) by macrophages (FIGS. 18D-18F). FIG. 18F shows that gold nanoparticles (Au-NPs) are released from the nanoclusters within the macrophages.

Figure 4A:
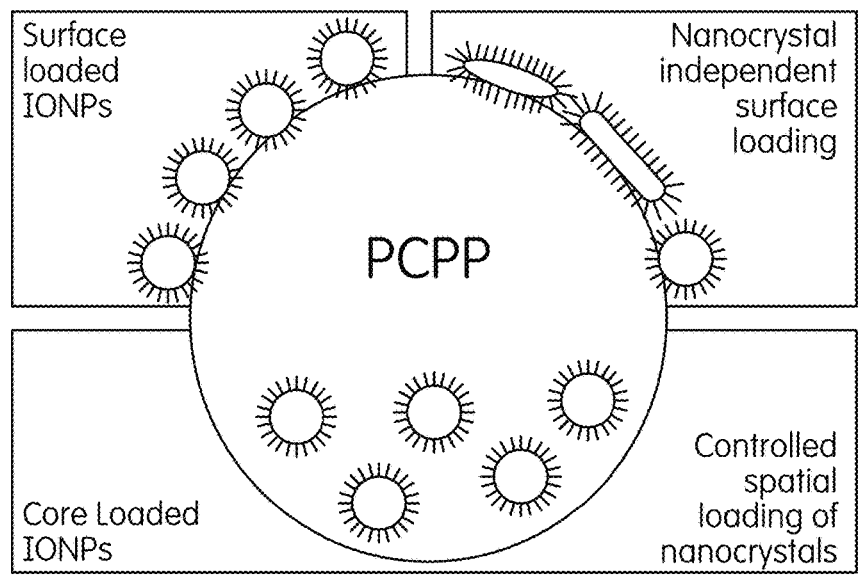
FIG. 4 shows a schematic of a nano-disco ball with surface-loaded nanocrystals.
Figure 4B:
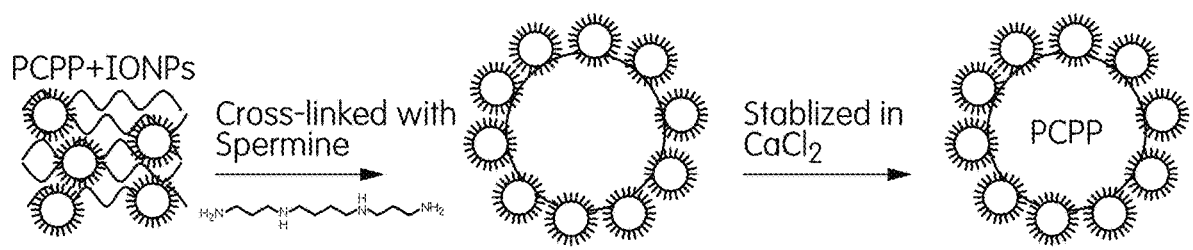

According to at least one embodiment, the nanocrystals can be selectively loaded onto the surface of polymer nanospheres. This forms a structure reminiscent of a disco ball, which we term a "nano-disco ball," a schematic of which is shown in FIG. 4. We have found that phospholipid coated inorganic nanoparticles can be used to surface decorate a polymer nanosphere formed from PCPP.

We studied the mechanism of this loading phenomenon and whether excess phospholipids could prevent nanocrystal adherence. We found surface loading to occur with a variety of nanocrystal types including iron oxide nanoparticles, quantum dots, and nanophosphors, as well as sizes (10-30 nm). Additionally, surface loading occurred over a range of polymer molecular weights (~30-3,000 kDa) and phospholipid carbon tail length, demonstrating the broad applicability of the platform. The nanocrystals remained diagnostically active after loading onto PCPP nanospheres, i.e., magnetic resonance imaging contrast for iron oxide nanoparticles and fluorescence for quantum dots. PCPP nanospheres surface loaded with IONPs showed structural stability when incubated for four hours in serum or with a monocyte cell line.

Another aspect of the present invention relates to tracking of cells (e.g., monocytes) using the nanoclusters described above.

According to at least one embodiment, monocytes are incubated with nanoclusters containing a diagnostically active agent. The monocytes are then injected in a subject and the subject is then scanned.

Another aspect of the present invention relates to tracking drug delivery. Nanoclusters comprising both a diagnostically active agent and a drug, or mixtures of nanoclusters separately containing a diagnostically active agent and a drug can be injected in a subject and then the subject scanned to ensure that the drug is delivered to the desired location. Upon degradation of the polymer encapsulant, the drug is then released in the desired location.

In another aspect of the present invention, the nanoclusters could be used as therapeutic adjuvants. For example, the nanoclusters could be used to enhance the effect of radiation therapy by increasing the radiation absorbed in a diseased site. Alternatively, the nanoclusters could be used in photothermal ablation or other ablation techniques where the nanoclusters would preferentially absorb electromagnetic radiation such as near infra-red light and convert it to heat, thereby resulting in pathological tissue death.

EXAMPLES

Materials

Poly(bis(4-carboxyphenoxy)phosphazene) disodium salt (PCPP, 1 MDa) was purchased from Sigma-Aldrich (St. Louis, Mo.). PCPP polymers of 3.8 MDa and 36.4 kDa molecular weight were synthesized at Pennsylvania State University. All phospholipids including 1-myristoyl-2-hydroxy-sn-glycero-3-phosphocholine (MHPC) and chain length variants were purchased from Avanti Polar Lipids (Alabaster, Ala.). Oleic acid capped cadmium sulfide quantum dots were purchased from NN-Labs, LLC (Fayetteville, Ark.). Oleic acid capped iron oxide nanoparticles (IONPs) of various sizes (10, 15, 20, 25, 30 nm) were purchased from Ocean NanoTech (Springdale, Ark.) and some IONPs were synthesized at University of Pennsylvania (vide infra). All other chemicals of analytical grade were purchased through Sigma. Aldrich (St. Louis, Mo.) with the exceptions of sodium fluoride (Acros Organics, NJ), trifluoroacetic acid (Alfa Aesar, MA), Tetrahydrofuran (EMD, PA), dichloromethane (EMD, PA), and ethyl ether (EMD, PA). Gadolinium or lanthanum trifluoroacetate precursors were prepared using a literature method by refluxing gadolinium or lanthanum oxide in trifluoroacetic acid/water mixture (50 vol %). A monocyte cell line, RAW 264.7, was purchased from ATCC. Cells were cultured in Dubecco's Modified Eagle Medium supplemented with 10% fetal bovine serum and 1% penicillin/streptomycin (10,000 units/mL, 10,000 μg/mL) from Life Technologies Invitrogen (Grand Island, N.Y.).

Polyphosphazene Synthesis

For 35.6 kDa PCPP preparation, $PCl_5$ (0.11 g) was dissolved in 50 mL anhydrous dichloromethane (DCM) for 10 min. Chlorophosphoranimine (6.00 g) was added to the solution rapidly, and the reaction was stirred at room temperature for 4 hr. DCM was then removed under reduced pressure to give colorless viscous living oligo(dichlorophosphazene). The polymer was re-dissolved in anhydrous tetrahydrofuran (THF), and propyl 4-hydroxybenzoate (14.43 g) and $CsCO_3$ (26.00 g) was added to the solution. The mixture was allowed to stir at room temperature for 2 days. Afterwards, the reaction medium was concentrated and precipitated into water (300 mL×3). The precipitate was isolated by centrifugation. Then, the crude product was re-dissolved in DCM, and dialyzed versus methanol/DCM (1:4) for 3 days (Spectra/Por dialysis membrane, MWCO: 1,000). The solvent was removed under vacuum to give a white sticky polymer. (Molecular weight: 35.6 g/mol; PDI: 1.07; repeat units: 82) For the deprotection reaction, the above 1.00 g of polymer was dissolved in 100 mL anhydrous THF. Potassium tert-butoxide (2.50 g) and water (0.45 g) were added to the polymer solution. The reaction was stirred at room temperature for 3 days. After that, the reaction medium was dialyzed versus water for 1 day, water/methanol (1:1) for 2 days, and then methanol for 2 days (Spectra/Por dialysis membrane, MWCO: 1,000). Poly(bis(4-carboxylatophenoxy)phosphazene) dipotassium was obtained by the removal of all solvent under vacuum at 35° C. (overall yield: 46%). $^{31}P$ NMR ($D_2O$): δ −18.75 (s). $^1H$ NMR ($D_2O$): δ 7.31 (d, 2H), 6.50 (d, 2H).

A high molecular weight (MW) PCPP (3.8 MDa) was synthesized by first dissolving poly(dichlorophophazene) (2.00 g) in 200 mL of THF. Poly(dichlorophosphazene) was prepared by the thermal ring-opening polymerization of recrystallized and sublimed hexachlorocyclotriphosphazene (Fushimi Chemical Co., Japan) in evacuated Pyrex tubes at 250° C. Propyl-4-hydroxy-benzoate (9.33 g) was dissolved in THF (100 mL) then added to the polymer solution. Solid cesium carbonate (16.9 g) was then immediately added to the reaction mixture. The reaction proceeded at room temperature for 3 days. Afterward, the solution was concentrated, and precipitated into water 3 times and hexane once. The solvent was removed under reduced pressure to yield a white solid that was obtained in an 80% yield (molecular weight: 3,882,000 g/mol; PDI: 1.62; repeat units: 9,600). For the de-protection reaction, the polymer (3.00 g) was re-dissolved in anhydrous THF (300 mL). Potassium tert-butoxide (7.51 g) and water (1.34 g) were added to the polymer solution. The reaction was stirred at room temperature for 3 days and was then concentrated. This was dialyzed versus water for 2 days, (1:1) methanol/water for 2 days, and then (4:1) methanol/water for 1 day. The solvent was then removed under reduced pressure to yield the product with an 81% yield. $^{31}$P NMR (D2O): δ −18.53 (s). $^1$H NMR (D2O): 7.16 (s, 2H), 6.36 (s, 2H).

Iron Oxide Synthesis

Iron oxide nanoparticles (IONPs) were synthesized using oleic acid as the capping ligand. Typically, 1.5 g of iron chloride and 5.2 g of sodium oleate were first added in a 100 mL flask. Subsequently, 20 mL of hexane, 11.5 mL of ethanol, and 8.8 mL of distilled water were added to the flask and the mixture was sonicated. The two-phase mixture was heated to reflux (~70° C.) for four hours, which produced iron-oleate in the organic layer. The upper organic layer was washed three times with 30 mL of water and separated by centrifugation (5,000 rpm, 10 min). After washing, the hexane was evaporated from the dark brown organic layer and stored under vacuum. The synthesis of 15.6 nm iron oxide nanoparticles was carried out by reacting 5.5 g of iron-oleate and 1.5 g of oleic acid in 31 g of 1-octadecene in a 250 mL round-bottom flask. The reaction mixture was heated to 320° C. at a rate of 200° C./hour, and kept at that temperature for 30 minutes. The color of the solution turned from dark brown to black upon the formation of nanoparticles. The resulting solution was cooled to room temperature and nanoparticles were precipitated by adding ethanol (35 mL). The precipitated nanoparticles were collected by centrifugation (5,000 rpm, 10 mins) and then redispersed in hexane (10 mL). The nanoparticles were further purified by precipitation with acetone (35 mL), centrifuging at 5,000 rpm for 10 min, and redispersing the collected nanoparticles in hexane (10 mL). This washing step was repeated two more times. After the final washing step, the IONPs were redissolved in chloroform (10 mL) and centrifuged at low speed (3,000 rpm, 5 min) to remove aggregates. A sample of these IONPs was rendered water soluble through encapsulation with dimercaptosuccinic acid (IO-DMSAs).

Nanophosphor Synthesis

Gadolinium nanospheres (GdF$_4$) were synthesized. Briefly, gadolinium trifluoroacetate (2 mmol) and sodium fluoride (5 mmol) were added into a 125 mL three-neck flask containing 60 mL of 1-octadecene/oleic acid solvent mixture (50% by volume). The solution was then degassed under vacuum at 125° C. for an hour to remove water. For nanocrystal growth, the solution was heated to 290° C. under N$_2$ environment at a rate of 10° C./min and maintained at this temperature for 5 hours. Purification was performed twice by washing with ethanol and then centrifuging at 6000 rpm for 2 min. Gadolinium nanorods (GdF$_4$) were synthesized by using lithium fluoride (6 mmol) instead of sodium fluoride in the method. LaF$_3$ discs were synthesized using similar methods as NaGdF$_4$ nanorods while substituting lanthanum trifluoroacetate for gadolinium trifluoracetate. LaF$_3$ nanoplates were redissolved in hexane and centrifuged at 3000 rpm for 2 min to remove lithium fluoride salts.

Nanocrystal Micelle Synthesis

IONPs, quantum dots, and nanophosphors were rendered water soluble through encapsulation in phospholipid micelles. In a typical preparation, 50 mg of MHPC was dissolved in a 1 mL chloroform/methanol mixture (4:1). Oleic acid coated IONPs (5.00 mg in 0.5 mL chloroform) were added to the MHPC solution. This mixture was then added to heated Milli-Q water (10 mL) in a slow, drop-wise fashion. The resulting solution was heated for an additional 10 min to ensure organic solvent evaporation and then cooled to room temperature. Afterwards, the aqueous solution was centrifuged at 800 g for 10 min to remove precipitates and multi-cored micelles. The supernatant was collected and centrifuged at 20,000 g for 90 min. The pellet was redispersed in Milli-Q water (~15 mL). These washes were performed three times to ensure purification. Finally, the sample was resuspended in approximately 1 mL of Mill-Q water yielding IONPs encapsulated in MHPC micelles (IO-MHPCs). Quantum dots and nanophosphors were encapsulated using similar methods as the IONPs. Iron oxide encapsulation was also performed using the following additional lipids: 1-lauroyl-2-hydroxy-sn-glycero-3-phosphocholine (IO-LHPCs), 1-palmitoyl-2-hydroxy-sn-glycero-3-phosphocholine (IO-PHPCs), and 1-stearoyl-2-hydroxy-sn-glycero-3-phosphocholine (IO-SHPCs). Additionally, MHPC micelles were formed in the absence of any nanocrystals to obtain samples of empty MHPC micelles. Mixed phospholipid micelles encapsulating IONPs (10, 15, 20, 25, and 30 nm diameter) were formed with a 1:1 mixture of MHPC and dimyristoyl-2-hydroxy-sn-glycero-3-phosphocholine (IO-MHPC-DMPCs).

PCPP Sphere Synthesis

Formation of polyphosphazene polymer nanospheres was performed. A typical synthesis was performed as follows, 40.0 mg of PCPP (1.0 MDa MW) was dissolved in 20 mL of Dulbecco's phosphate buffered saline (DPBS, pH 7.4). IO-MHPCs (0.15 mg, 200 ul) were added into 1 mL of this PCPP solution. Then 16.8 μL of a 70.0 mg/mL spermine solution (DPBS, pH 7.4) was added to the PCPP/IO-MHPCs solution (0.98% spermine). The mixture was immediately added into a beaker of 88.0 mg/mL CaCl$_2$ buffer (~100 ml) and incubated at room temperature for 30 minutes while stirring. This suspension was purified through centrifugation (800 g, 10 min) and washed three times with Milli-Q water. The resulting IO-MHPCs surface loaded nanospheres (IO-NBs) were resuspended in 1 mL of Milli-Q water. This process is depicted schematically in FIG. 1b. Synthesis of non-loaded PCPP nanospheres were formed identically, except without the addition of IO-MHPCs. Nanocrystal variants such as CdS quantum dots and nanophosphors (GdF$_4$ spheres, GdF$_4$ rods, LaF$_3$ discs), or iron oxides or varying cores sizes and coating types were substituted for IO-MHPCs for inclusion in the PCPP nanosphere synthesis. PCPP of additional molecular weights (35.6 kDa and 3.88 MDa) were also used to form surface loaded nanospheres.

Polymer and Particle Characterization $^1$H and $^{31}$P NMR spectra were recorded on a Bruker WM-360 NMR spectrometer operated at 360 and 145 MHz, respectively. $^1$H NMR spectra were referenced to solvent signals while $^{31}$P NMR chemical shifts were relative to 85% phosphoric acid as an external reference, with positive shift values downfield from the reference. Molecular weights were estimated using a Hewlett-Packard HP 1090 gel permeation chromatograph (GPC) equipped with an HP-1047A refractive index detector, American Polymer Standards AM gel 10 mm and AM gel 10 mm 104 Å columns, and calibrated versus polystyrene standards.

Transmission electron microscopy images were acquired on a FEI Tecnai T12 microscope at 120 kV. Scanning electron microscopy was performed with a Philips XL20 at 10 kV. Fluorescent imaging was performed with an IVIS Spectrum system using a 465 nm excitation and 520 nm emission filter. Relaxivities were measured using a Bruker Minispec mq relaxometer at 1.41 T (60 MHz) and 40° C. Freely suspended IO-MHPCs were prepared in DPBS for measurements. PCPP samples were prepared in a 1% agar gel in DPBS to prevent sedimentation of nanospheres. Iron oxide concentrations were determined through inductively coupled plasma-optical emission spectroscopy (ICP-OES) on a Spectro Genesis system.

Magnetic resonance imaging (MRI) was used to evaluate IO-NBs contrast generating properties. IO-NBs were prepared in a 1% agar gel at concentrations of 0.05 mM and 0.16 mM of Fe. Additionally, control samples of DPBS, non-loaded PCPP, and 0.16 mM of Fe IO-MHPCs in 1% agar gel were scanned. For MRI phantom preparation, samples were placed in a 2% agar gel doped with 0.35 mM manganese chloride. The samples were scanned using a head coil on a Siemens Magnetom Trio with a 3 T magnet. A 2D spin echo sequence was used. Relevant imaging parameters were: echo time (TE), 15 ms; repetition time (TR), 10 s; 1 slice with thickness 3 mm, 1 average, flip angle (FA), 90 degrees; acquisition matrix, 184×256; in-plane spatial resolution 0.546 mm$^2$, field of view (FOV) 140 mm$^2$. The resulting images were processed using Osirix v.3.0.1 32-bit (Geneva, Switzerland; www.osirix-viewer.com).

In Vitro Cell Studies

RAW 264.7 cells were cultured on 6-well plates at a concentration of 2 million cells/mL at 37° C. After 24 hours, the cells were treated with IO-NBs at a concentration of 50 µg Fe/mL (0.89 mM) for 4 hours. The cells were washed 3 times with DPBS and then collected by gently scraping. The cells were fixed in a solution of 2% glutaraldehyde and 5% paraformaldehyde in DPBS. Fixed cells were embedded in resin and prepared for TEM using standard methods. Cell sections were imaged using a FEI Tecnai T12 electron microscope.

Results

Surface Decoration of PCPP Nanospheres

PCPP is a biocompatible polymer, which we have used to create a novel platform to exploit for nanocrystal delivery in biomedical applications. PCPP nanospheres were synthesized. The polycarboxylate PCPP is cross-linked with the polycation spermine to form polymer spheres. The self-assembled nanospheres were dispersed in CaCl$_2$ to stabilize the spheres. This process resulted in polymer nanoparticles of 508±185 nm (FIG. 1a). As an initial step in loading these polymer nanoparticles, we added dimercaptosuccinic acid coated iron oxides (IO-DMSAs) to the synthesis prior to adding the spermine cross-linker. We found that IO-DMSAs were included in the polymer spheres in their cores (FIG. 5b). We then decided to explore the incorporation of iron oxide nanoparticles with alternative coatings.

Oleic acid coated nanocrystals were rendered water soluble through encapsulation in micelles formed by MHPC. These phospholipid coated nanocrystals were mixed with PCPP before the addition of spermine. In the final product the nanocrystals were exclusively localized to the surface of the nanospheres, in a structure reminiscent of a disco ball (FIG. 5c, d). Electron microscopy images of these IO-MHPCs surface loaded PCPP nanoparticles, or nano-disco balls (IO-NBs), can be seen in FIG. 5c. The average diameter of IO-NBs was found to be 384±127 nm (from analysis of 100+ nanoparticles in TEM images). SEM images revealed IO-NBs to be an average diameter of 473.7±125.9 nm and non-loaded PCPP nanospheres to be 548.7±200.8 nm. (FIG. 5e, f). Three dimensional tomographic reconstructions were performed to confirm the localization of IO-MHPCs with PCPP nanoparticles. The reconstructions proved exclusive loading of IO-MHPCs on the surface of PCPP nanospheres (FIG. 5g, h).

Surface Adhesion Occurs During Stabilization with CaCl$_2$

The surface loading of PCPP nanospheres occurs in a self-assembled manner during synthesis. To investigate the crucial synthesis step in the formation of surface loaded nanospheres, IO-MHPCs were added at different points in the process. Initially, IO-NBs were formed by mixing IO-MHPCs with a PCPP solution and then adding spermine as schematically outlined in FIG. 4b. The mixture was quickly transferred to a CaCl$_2$ solution and incubated at room temperature for 30 minutes. Afterwards the solution was washed through centrifugation and resuspended in water. To determine if longer incubations of IO-MHPCs and PCPP solution together would result in internal loading of IO-MHPCs, the reagents were incubated together at room temperature for 30 minutes and 24 hours before the addition of spermine. Results in FIGS. 6a and 6b show no visible differences between our standard synthesis and the 30 minute pre-incubation. Additionally, the 24 hour pre-incubation sample showed similar structure to 30 minute pre-incubation method indicating that longer incubation times do not affect spatial distribution of IO-MHPCs in PCPP nanospheres.

Next we examined the effect of mixing PCPP with spermine before the addition of IO-MHPCs. As shown in FIG. 6c, IO-MHPCs surface adherence was unaffected when added after spermine addition, demonstrating that surface loading does not occur during the PCPP and spermine cross-linking process. To further explore the mechanism of surface loading, non-loaded spheres were completely formed before the addition of IO-MHPCs. The PCPP solution and spermine were first mixed and then transferred to CaCl$_2$ for 30 minutes at room temperature. Afterwards, IO-MHPCs were added into the solution and stirred for an additional 30 minutes. The results seen in FIG. 6d showed no surface loading of IO-MHPCs in the sample. These data demonstrate that surface loading of MHPC lipid coated IONPs (IO-MHPCs) is achievable at any stage before CaCl$_2$ stabilization.

Figures 8A, 8B:
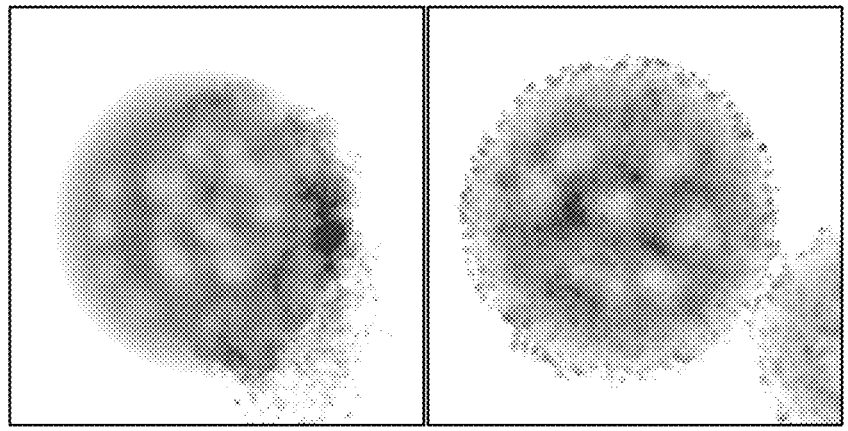
FIG. 8 shows electron microscopy images of PCPP nanospheres with increasing carbon tale lengths.
Figures 8C, 8D:
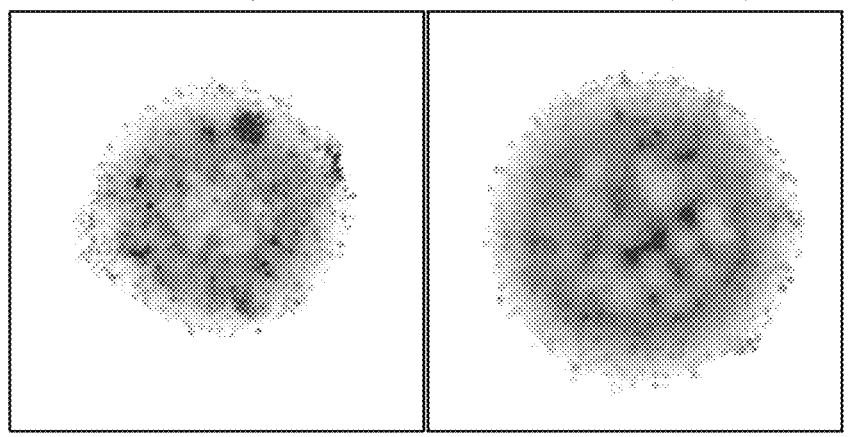
Figures 9A, 9B:
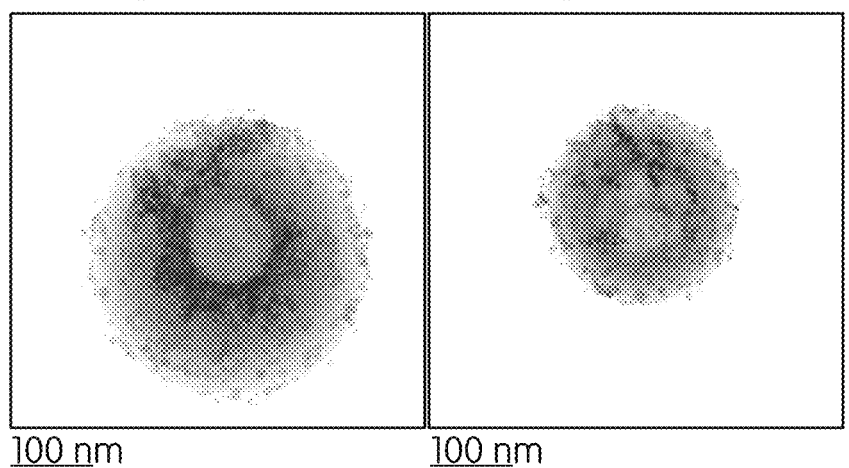
FIG. 9 shows electron microscopy images of PCPP nanospheres with different core sizes.
Figure 9C:
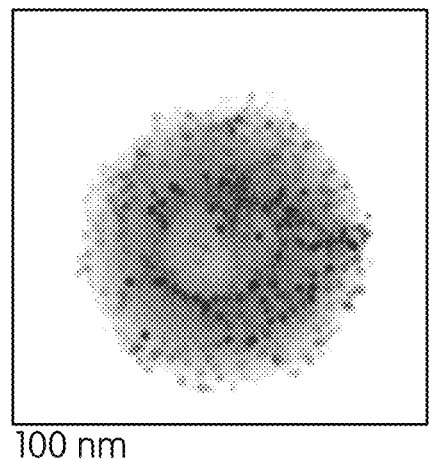
Figures 9D, 9E:
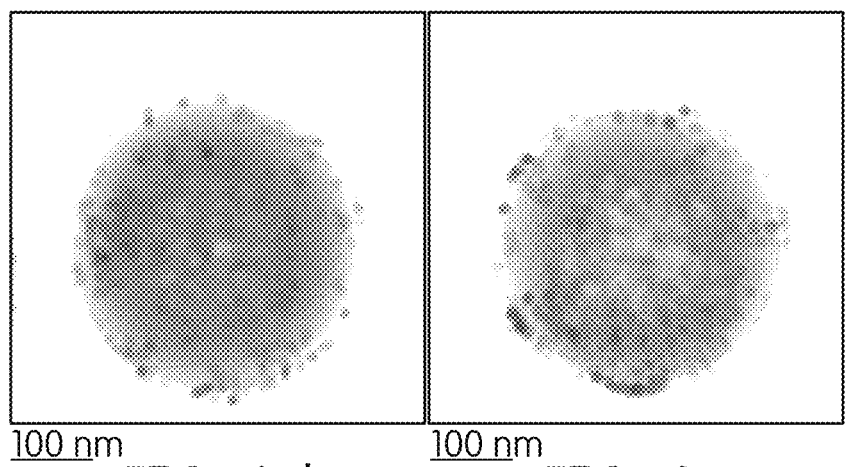

Surface Loading is Independent of Polymer Size, Lipid Length, Core Size, and Core Type Exclusive surface loading was found with the use of MHPC lipids encapsulating 15.6 nm diameter iron nanoparticles. The flexibility of the reaction was examined by varying parameters such as PCPP molecular weight, phospholipid length, and nanocrystal core size and type. Surface loaded nanospheres were synthesized using the standard method disclosed above with PCPP in a range of molecular weights (35.6 kDa, 1.0 MDa, 3.8 MDa MW). Surface loading of IO-MHPCs were found with each PCPP MW, demonstrating that the process is independent of polymer size (FIG. 7). The effect of phospholipid tail length was studied by encapsulating 15.6 nm diameter IONPs with 12 (LHPC), 14 (MHPC), 16 (PHPC), and 18 (SHPC) carbon tail chain length phospholipids. PCPP nanospheres were successfully synthesized and surface loaded with each micelle formation (FIG. 8. Note that LHPC is a relatively poor amphiphile, which resulted in aggregates as opposed to individually dispersed nanocrystals). Additionally, oleic acid IONPs of increasing sizes (10, 15, 20, 25, 30 nm diameters) were encapsulated in micelles using MHPC/DMPC mixtures. Micelles synthesized using only MHPC to encapsulate the larger 25 and 30 nm IONPs were not stable, however, they could be stably coated with a 1:1 mixture of MHPC/DMPC and that nanoparticles with such coatings adhered to PCPP nanospheres also. The PCPP nanospheres were synthesized using the standard method above with the various IONP core sizes. TEM revealed surface loading was achievable with each core size (FIG. 9).

To further explore the breadth of applicability for this process, a variety of diagnostically active nanocrystals were investigated for adherence to PCPP nanospheres. Oleic acid coated quantum dots (CdS spheres) and nanophosphors (GdF$_4$ spheres, rods, LaF$_3$ discs) were all found to incorporate into MHPC micelles using the same procedure as for IONPs. Surface loading of each core variant was achieved through our standard method of PCPP nanosphere synthesis. TEM verified surface adsorption to be present in each sample (FIG. 10). From these data, nanocrystals encapsulated into phosphocholine head group lipid micelles result in successful surface adsorption regardless of the core type, size, or shape.

Excess Empty Micelles Disrupt Nanosphere Formation but not Surface Adherence

Figures 11A, 11B:
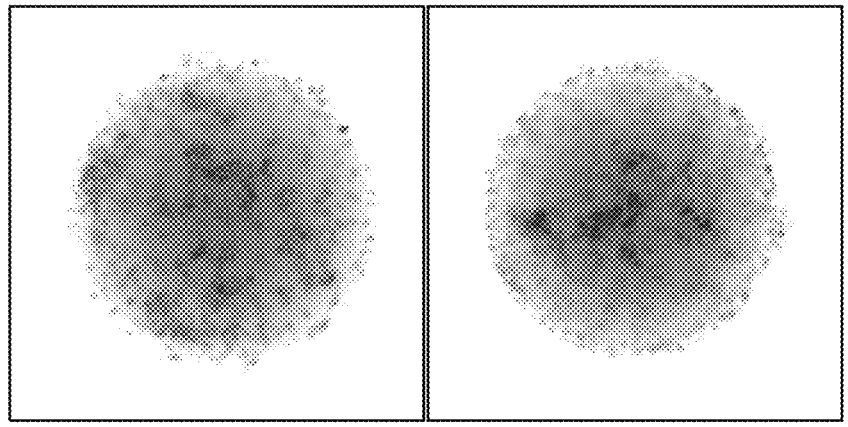
FIG. 11 shows electron microscopy images of PCPP nanospheres with empty micelles.
Figures 11C, 11D:
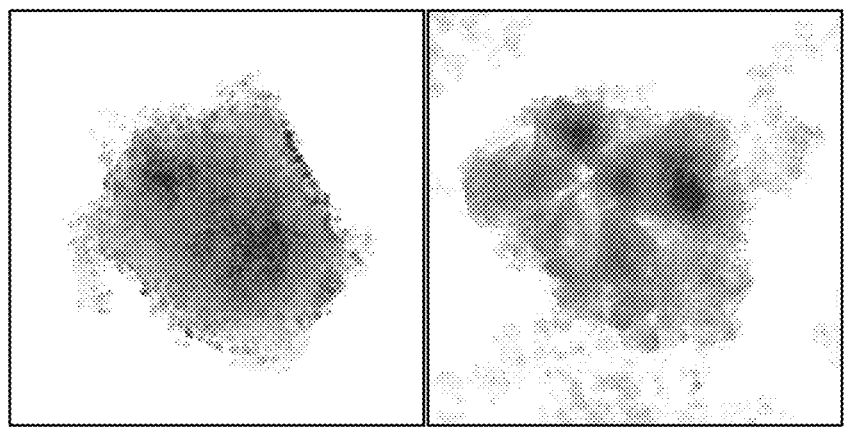

Whether an excess of empty micelles would reduce surface adsorption of IO-MHPCs on PCPP nanospheres was examined. Empty MHPC micelles were mixed together with IO-MHPCs at increasing ratios (1:1, 5:1, 10:1, 25:1, based on phospholipid content). PCPP nanosphere synthesis was performed using our standard method with these empty micelles:IO-MHPCs ratios. From TEM, lower ratio mixtures did not appear to affect surface adsorption of IO-MHPCs onto the PCPP nanospheres (FIG. 11). However, at larger ratios of 10:1 and 25:1, disruption of nanosphere formation was observed. These particles appeared amorphous but the surface adsorption of the IO-MHPCs was still present. The increased concentration of empty micelles appeared to interfere with the spermine-PCPP cross-linking. We hypothesized that performing the cross linking before the addition of IO-MHPCs and empty micelles would allow for the observation of competition without disrupting the PCPP nanosphere formation. We found that by adding in the spermine before the IO-MHPCs, we were able to surface load IO-MHPCs in the presence of high concentrations of empty micelles. Ratios of 10:1, 15:1, 20:1, 25:1 were used in the synthesis, and surface loading of IO-MHPCs appeared similar in all samples. This phenomenon could be due to the larger area of interaction for the IO-MHPCs with the PCPP nanospheres could create stronger attachments, leading to preferential binding of IO-MHPCs as compared to empty MHPC micelles.

Particles Remain Diagnostically Active after Surface Loading

Figure 12A:
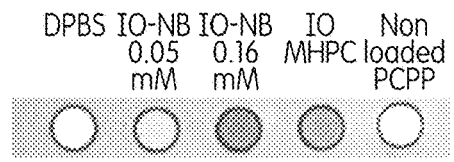
FIG. 12 shows applications of surface loaded PCPP nanospheres.
Figure 12B:
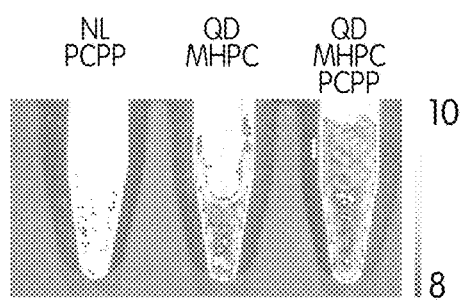

With the ability to load a variety of diagnostically active nanoparticles, the contrast generating properties of nanocrystal loaded polymer particles was evaluated. The longitudinal and transverse relaxivity (measures of MRI contrast) of surface loaded IO-NBs was examined (Table 1). Surface loaded particles, IO-NBs were found to have a lower transverse ($r_2$) relaxivity than free IO-MHPCs, although still at a substantial value of 68.2 mM$^{-1}$s$^{-1}$. The decreased relaxivity could be due to the loss of interaction between the surrounding water and the surface adsorbed IO-MHPCs due to the adsorption to PCPP nanospheres. However, the ratio of transverse to longitudinal relaxivity ($r_2/r_1$) was higher for IO-NBs indicating good properties for T2-weighted imaging. Additionally for further evaluation, contrast generation for IO-NBs was evaluated with a MRI scan. Iron oxide increases the rate of transverse relaxation therefore leading to a decrease in signal intensity, or darkening in $T_2/T_2^*$-weighted MR images. An MR image of a phantom containing IO-NBs (0.05 and 0.16 mM Fe), DPBS, free IO-MHPCs (0.16 mM Fe) and non-loaded PCPP spheres is displayed in FIG. 12a. The DPBS and non loaded PCPP nanospheres were of relatively similar signal intensity. As expected, the IO-NBs were much darker, with a concentration dependent intensity. Although, the IO-NB and IO-MHPC samples were at the same concentration, the IO-NBs produced less signal. This effect could be due to the increased relaxivity ($r_2/r_1$) ratio seen in the relaxation measurements, or perhaps is due to the different field strengths used for imaging and to determine relaxivities. Overall, IO-NBs retained relaxation properties that allow for contrast generation in MRI. Moreover, PCPP nanospheres loaded with quantum dots (QD-NBs) exhibit similar fluorescent properties as free quantum dots (QD-MHPCs). The optical properties of the quantum dots persisted after encapsulation in micelles and PCPP surface loading (FIG. 12b).

TABLE 1

Relaxation measurements for free IO-MHPCs and IO-NBs.

| | $r_1$ (mM$^{-1}$s$^{-1}$) | $r_2$ (mM$^{-1}$s$^{-1}$) | $_2/r_1$ |
|---|---|---|---|
| IO-MHPCs | 3.95 | 107.66 | 7.3 |
| IO-NBs | 1.81 | 68.22 | 7.6 |

In Vitro Evaluation of Surface Loaded Nanospheres

Figure 12C:
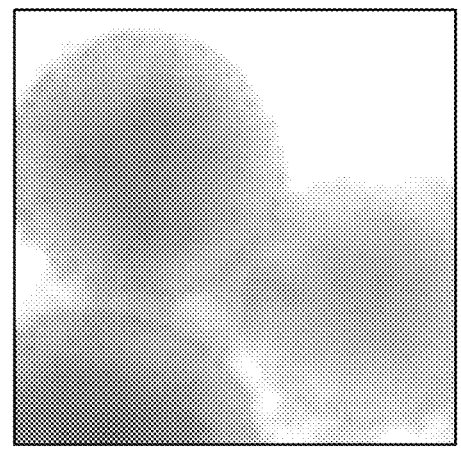
Figure 12D:
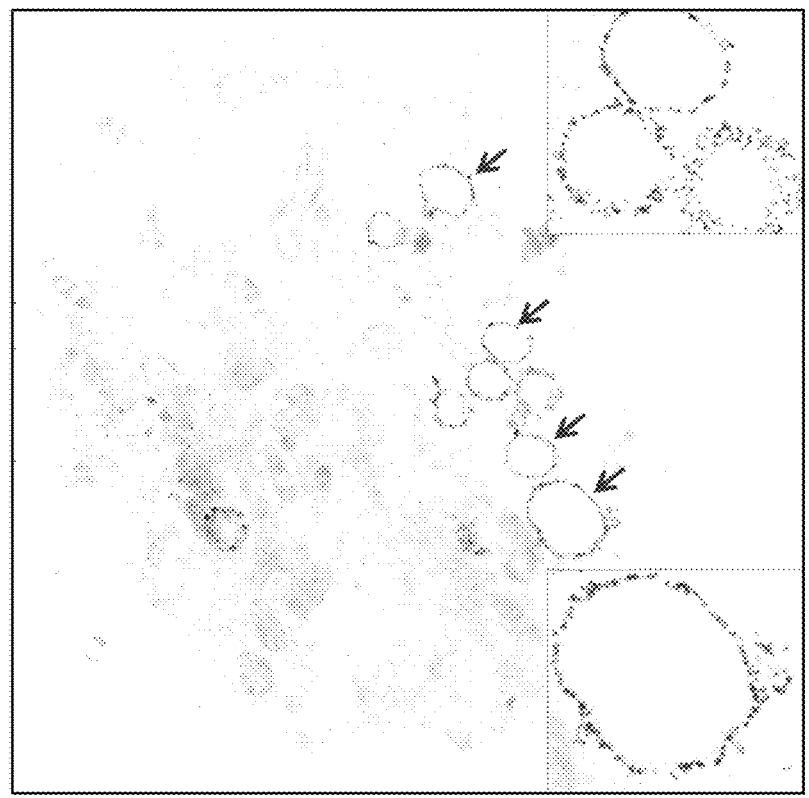

The robustness of surface attachment of IO-MHPCs to PCPP nanospheres was briefly evaluated for potential biological applications. First, nano-disco balls (IO-NBs) were incubated for 4 hr in cell culture media at 37° C. TEM performed on these nanoparticles revealed that many IO-MHPCs were still attached to the surface of PCPP nanospheres after this incubation (FIG. 12c). Next IO-NBs were incubated with RAW 264.7 monocytes for 4 hr. Remarkably, TEM performed on these cells revealed ring shaped organization of IO-MHPCs located within endosomes (FIG. 12d). We believe this demonstrates that the IO-MHPCs still remain surface bound to PCPP nanospheres after undergoing cellular uptake. The PCPP particles demonstrate retained surface loading over the time period tested.

Delivery of Protein Loaded IO-NB

With exclusive surface loading of polymer nanospheres, the internal core of the nanospheres can be used for drug loading. We used bovine serum albumin conjugated with fluorescein isothiocyanate (FITC-BSA, 0.25 mg) as a model drug. This was loaded into PCPP nanospheres (FITC-PCPP). Additionally, FITC-BSA was loaded into the core of nanospheres with simultaneous surface loading of IO-MHPC (FITC-NB, 0.1, 0.25 mg). TEM and fluorescence imaging were used to characterize FITC-PCPP and FITC-NB. Both particles demonstrated successful loading of FITC-BSA into the PCPP nanosphere as evident from the fluorescence of the purified material. TEM of FITC-NB revealed that IO-MHPC were surface loaded in the presence of the additional FITC-BSA payload, without alteration of the NB structure.

Figure 25:
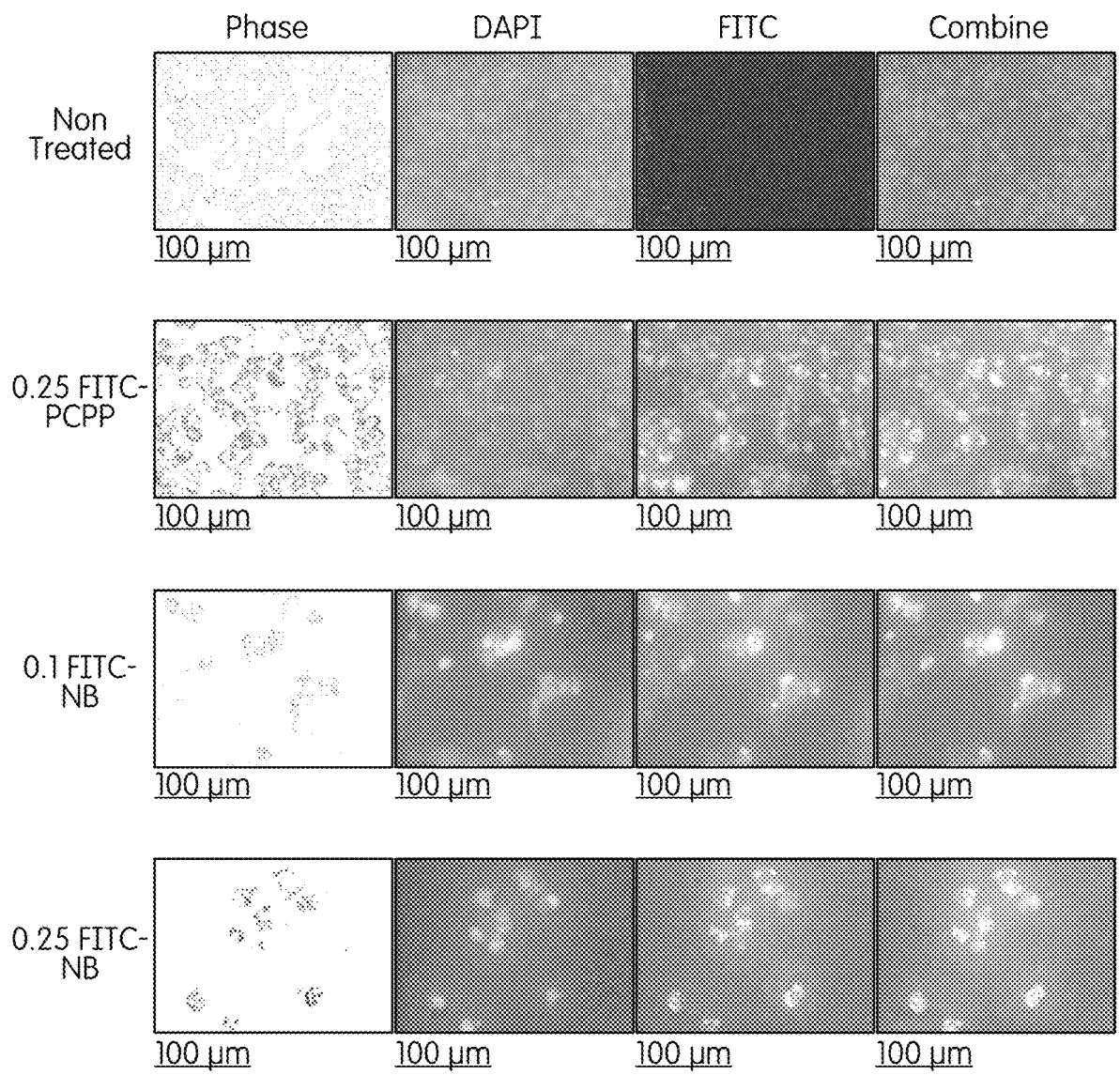
FIG. 25 shows the fluorescence of monocytes treated with FITC-BSA encapsulated PCPP nanospheres using DAPI, FITC, and a combination of DAPI and FITC.

To evaluate the ability of these particles to deliver FITC-BSA to cells, they were incubated with monocytes for 4 hours. Afterwards the cells were stained with DAPI and imaged with fluorescence microscopy. Phase images of treated cells reveal areas of particle uptake within the cells (FIG. 25). Additionally, FITC can be seen within the cells as defined by DAPI (nuclei stain). The added surface loaded IO-MHPC did not prevent the delivery of FITC-BSA to the cells. These data demonstrate that "drug" (FITC-BSA) loading can be achieved with additional exclusive surface loading. Furthermore, the loaded nanospheres remained stable for in vitro tracking of delivery into cells.

CONCLUSIONS

As described above, PCPP nanospheres can be loaded with nanocrystals in a controlled fashion to result in exclusive localization of the nanocrystals to the surface of the sphere rather than the typically observed core loading of polymer nanoparticles. A range of diagnostically active nanocrystals could be surface loaded onto the PCPP nanospheres regardless of their individual core size, shape, or chemical composition. The nanocrystals loaded on the spheres retained their contrast generating properties, i.e., MR contrast in respect to relaxation for iron oxide particles and fluorescence for quantum dots. The point of nanocrystal attachment was also probed through the investigation of each synthesis step. It was observed that surface loading was successful prior to $CaCl_2$ addition. In addition, it was found that surface loading was achievable using a variation of polymer sizes and phospholipid tail lengths, demonstrating multiple feasible approaches to surface loading. A robust and unique platform for surface localization of nanoparticles onto a polymeric sphere to form 'nano-disco balls' is described.

We also found that simultaneous surface and core loading is possible. We showed the stability of the nano-disco balls in cell culture media and the potential for drug delivery applications. The generation of multimodal contrast agents could be achieved by controllably loading separate agents into the core and surface of these PCPP spheres. Moreover, selective loading into the core and surface presents new opportunities in the areas of drug delivery and theranostics.

Gold Nanoparticle-Containing Nanoclusters

Generation of Library

A library of biocompatible, sub-5 nm gold nanoparticles will be synthesized and evaluated as CT contrast agents and for excretion. Gold nanoparticles will be synthesized with a variety of small molecule coatings that render solubility in biological media and should be non-toxic. Nanoparticles whose diameter is found to be less than 5 nm and are found to be non-toxic via in vitro biocompatibility assays will be tested for their in vivo vascular CT contrast properties in both wild type mice and a chronic kidney disease model. Excretion will be screened for with analytical techniques. In vivo toxicity will be studied with histology and blood markers.

Encapsulation of Gold Nanoparticles

Small gold nanoparticles will be encapsulated into slow-releasing polyphosphazene polymer and evaluated as CT contrast agents and for excretion. The three best excreted gold nanoparticle formulations identified above will be encapsulated into polyphosphazene nanospheres. Inclusion efficiency will be optimized via adjusting the conditions and varying the polymer composition. Gold nanoparticle release and biocompatibility will be assessed in vitro. The aim will be to identify carrier structures that provide high encapsulation and slow release (>24 hours). Vascular CT contrast generation and excretion will be studied with the methods outlined above.

Biodegradable Gold Nanoparticles

In this application we propose to create a novel nanoparticle system where the above-mentioned sub-5 nm gold nanoparticles that are excretable and biocompatible are encapsulated in a nanoparticle composed of a hydrophilic, biodegradable polymer, i.e. a polyphosphazene. This is a novel polymer for nanoparticle synthesis. We will mainly use di(carboxylatophenoxy)phosphazene (PCPP), which breaks down into phosphate, ammonia and 4-hydroxybenzoic acid (LD50 of 2200 mg/kg in mice), all biocompatible chemicals. Nanoparticles synthesized from hydrophobic polymers or oils that encapsulated metal nanocrystals have been previously reported, but the nanocrystals were hydrophobically coated. Breakdown of these nanoparticles in vivo would result in release of the hydrophobically coated nanocrystals, which would then immediately precipitate or be opsonized and not be excreted. Gold nanoparticles can be released from PCPP by diffusing out of the structure, by dissociation of the polymer aggregate or by hydrolysis of the polymer itself. The hydrophilic polyphosphazene nanoparticle approach allows for the encapsulation of hydrophilically-coated nanocrystals that, when the nanoparticle degrades, will mix with blood or other bodily fluids and can be excreted via the kidneys. The gradual release of gold nanocrystals from these polymer nanoparticles should result in a minimal impact on kidneys. Once this platform is established, it could used for future applications via addition of targeting ligands, or by encapsulation of alternative cargoes, such as quantum dots or drugs. Notably, this platform could also be used to encapsulate other, cheaper CT contrast core types such as bismuth. However, we propose a gold payload, as the well-developed chemistry of gold nanoparticles allows good synthetic control over their size and coating.

Approach

Synthesis of small gold nanoparticle coated with hydrophilic ligands that result in robust stability and biocompatibility is surprisingly poorly studied. Most work has been done with larger gold cores and large ligands such as PEG polymers. A library of sub-5 nm gold nanoparticles will be developed by using different coatings (FIG. 2) and study their biocompatibility. We will further evaluate their performance as CT contrast agents for vascular imaging and investigate their excretion in vivo.

Synthesis of a Library of Sub-5 nm Gold Nanoparticles

Figure 14A:
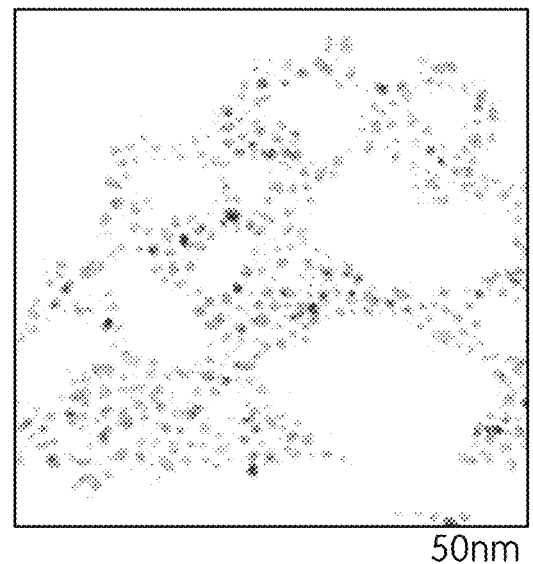
FIG. 14 shows a TEM of 5 nm gold nanoparticles coated with glutathione and the viability of macrophage cells incubated with the nanoparticles.

Gold nanocrystals will be synthesized via a modification of the method disclosed by Turkevich et al. (Turkevich, J., Stevenson, P. C., and Hillier, J. (1951) A study of the nucleation and growth processes in the synthesis of colloidal gold. Discuss. Faraday Soc. 11, 55-75), the disclosure of which is hereby incorporated in its entirety. In short, chloroauric acid will be reduced by addition of sodium borohydride. Surface modification of these nanocrystals is needed to provide stability in biological media. Incubation with the relevant ligand, followed by centrifugation will result in the desired end product (FIG. 14A). For example, 8 mg of $AuCl_3$ was dissolved in 100 ml of deionized water. 2 ml of sodium borohydride solution (5 mg/ml) was added dropwise, which resulted in the formation of a wine red solution. 1 ml of 17 mM glutathione was then added as a capping ligand. This resulted in gold nanoparticles whose average core size was 5 nm (FIG. 14A) and that were extremely stable in PBS. Certain ligands cannot easily be directly coated onto nanoparticles synthesized via the Turkevich method, in which case two-step substitution methods will be used where thioctic acid or Tween 20 is used as an intermediate coating in a two step substitution process. Alternatively, nanoparticles may be synthesized via direct reduction of gold salts in the presence of capping ligands. Last, gold cores could be synthesized by the method of Brust et al. (Brust, M., Walker, M., Bethell, D., Schiffrin, D. J., and Whyman, R. (1994) Synthesis of thiol-derivatised gold nanoparticles in a two-phase liquid-liquid system. Chem. Commun., 801-802), hereby incorporated by reference, where gold chloride salt is reduced with sodium borohydride in the presence of thiols. A relatively short chain thiol, such as heptanethiol, will be used, which will allow the coating to be substituted for a variety of molecules. After ligand substitution, the resulting nanoparticles will be isolated via centrifugation, washed and resuspended in deionized water.

The coating ligands will contain a thiol group at one end for binding to the gold surface and other functionalities, such as carboxylic acid groups, amines, amides and alcohols at the other end (FIG. 2). The chances of success with these ligands is high, as others have shown such ligands to be effective for producing small, stable and biocompatible nanoparticles that can be excreted via the urine. Single ligands as well as mixtures will be used, in order to create a diverse array of nanoparticle surface coatings. These ligands will provide solubility and stability in biological media, as well as will allow their incorporation into polyphosphazene particles under Aim 2. These nanoparticles will be characterized for size with transmission electron microscopy (TEM, FEI Tecnai T12), dynamic light scattering (DLS) and zeta potential (Zetasizer ZS90, Malvern Instruments).

Expected results: we expect that water soluble gold nanoparticles of <5 nm with a range of capping ligands can be synthesized.

Alternatives and pitfalls: Should the size limit not be met, smaller gold cores can be synthesized by using higher concentrations of capping ligands during synthesis—if the core is smaller, the overall nanoparticle size should be smaller. Our prior experience in this area and the results of others indicate that the proposed approaches should be successful.

Biocompatibility Evaluation

The gold nanoparticles will be tested for their stability in biological media by incubating with 10% serum for 24 hours and measuring their size with DLS. Biocompatibility will be assessed by incubating nanoparticles for two hours with SVEC4-10EHR1 (mouse endothelial cells), J774A.1 (mouse macrophage cells), HepG2 (hepatocytes) and Reneca (mouse epithelial kidney cells) at a range of gold concentrations, i.e. 0.005 to 1 mg Au/ml and performing the LIVE/DEAD assay to determine cell viability. Cells will be plated into 35 mm petri dishes that contain a 20 mm glass covered well for ease of use with a microscope. Cells will be incubated with gold nanoclusters as above, whereupon the media will be changed for media containing the LIVE/DEAD dyes. The cells will be incubated at room temperature for 30 minutes, washed with PBS and immediately imaged with a fluorescent microscope. The resulting images will be analyzed for red/green cells with a custom written Matlab program. Endothelial, macrophage, liver and kidney cells will be used as these cells should have greatest exposure to the gold nanoparticles upon injection. We will also perform these incubations with iopamidol, a clinically approved iodinated contrast agent. As an additional test, lysis of red blood cells will be examined, as will the viscosity and osmolality of injection strength solutions (250 mg Au/ml).

Figure 14B:
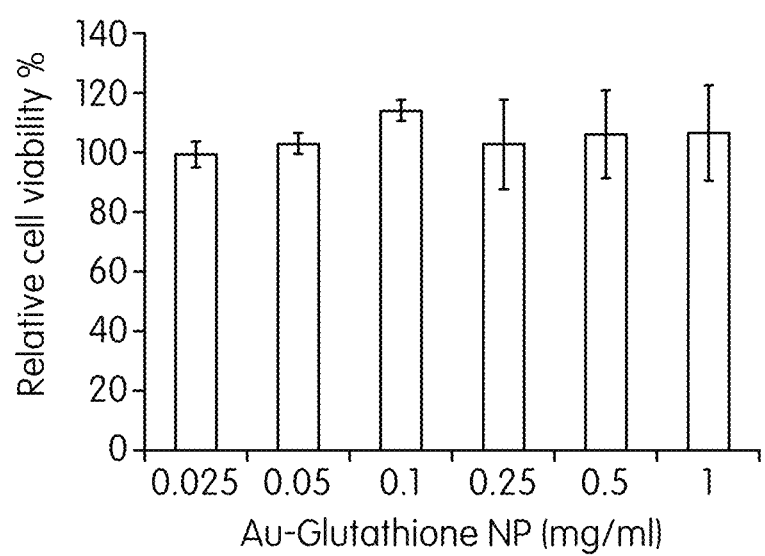

As an example, the biocompatibility of glutathione coated gold nanoparticles is shown in FIG. 14B. These nanoparticles were incubated with J774A.1 macrophage cells at a range of concentrations for 24 hours. Cell viability was not reduced even at concentrations as high as 1 mg/ml, indicating very high biocompatibility. These results demonstrate the ability to synthesize gold nanoparticles, to give them a highly stable coating and that such gold nanoparticles can be highly biocompatible.

Figure 22A:
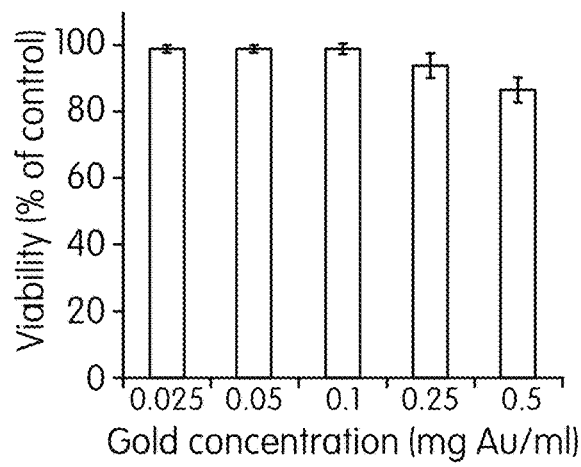
FIG. 22 shows (a) the effect of Au-PCPP on cell viability; (b) the viability measured at extended time points of cells incubated with Au-PCPP for 8 hours; and (c) the effect of Au-PCPP degradation products on cell viability.
Figure 22B:
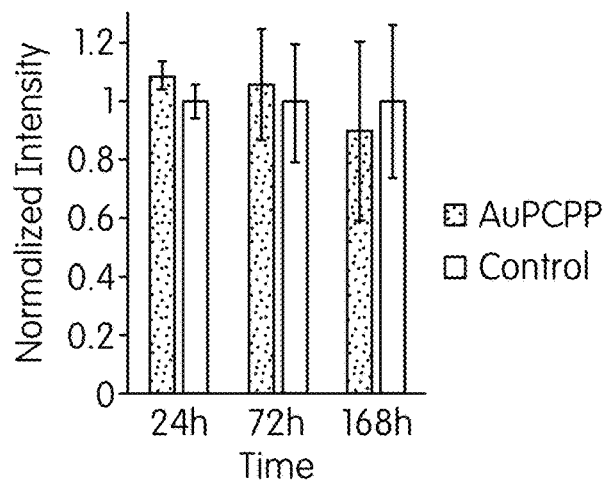
Figure 22C:
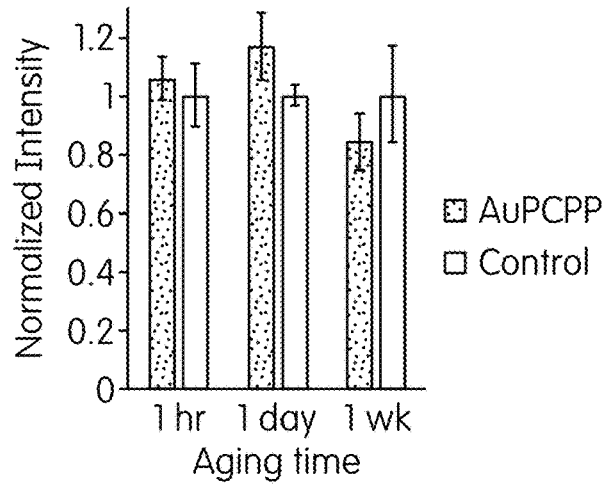

A second study of cell viability confirmed these results. FIG. 22A shows gold loaded PCPP-NP to be biocompatible even after incubation for 24 hours at 0.5 mg Au/ml with J774A.1 cells. No effect on HepG2 (hepatocyte) viability was seen at extended time points after incubation with Au-PCPP for 8 hours as shown in FIG. 22B. The toxicity of the Au-PCPP degradation products was also studied. FIG. 22C shows that there is no effect of Au-PCPP degradation products on HepG2 viability after aging for one week.

Expected results: Lead formulations will not increase in size more than 20% upon incubation with serum and will not lead to significant changes in cell viability or red blood cell lysis compared with control. The viscosity should be less than 25 cps, so as to be injectable under relevant flow rates (4 ml/s) and the osmolality should be no greater than that of 20% of blood (290 mOsm/kg).

Alternatives and pitfalls: Should the above tests be failed by all candidate nanoparticles, more candidates will be generated, exploring additional ligands, ligand combinations and nanoparticle sizes and evaluate those new formulations.

CT Contrast Properties, Excretion and In Vivo Biocompatibility

Figure 15:
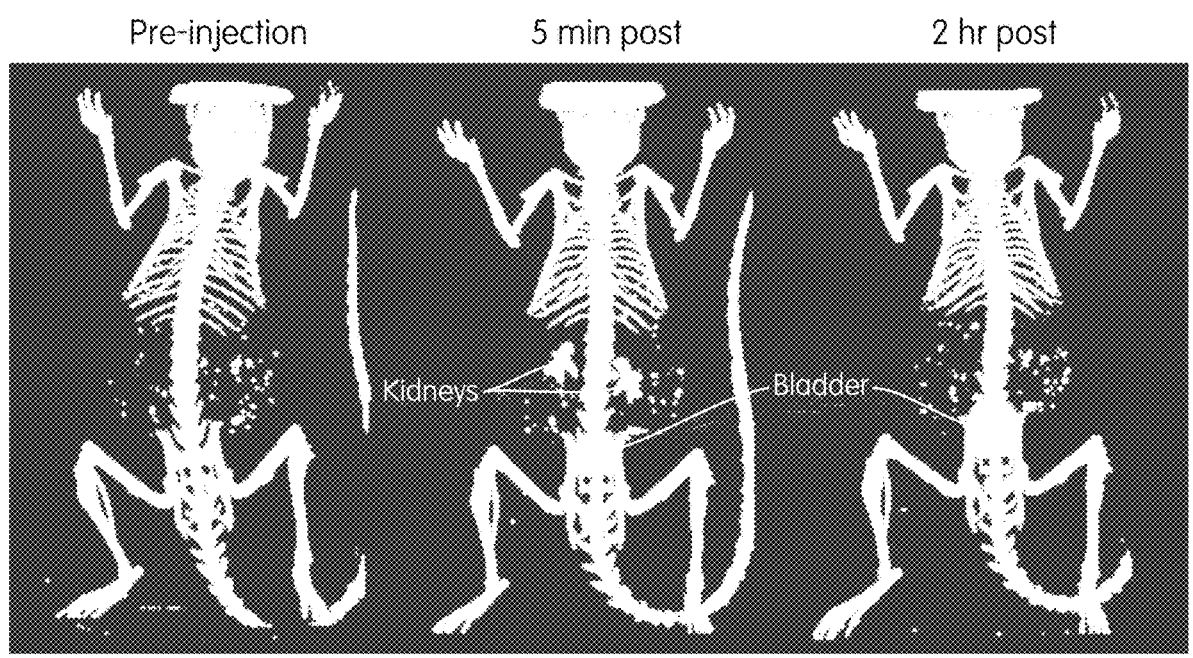
FIG. 15 shows microCT images of a mouse injected with glucose coated gold nanoparticles.

The CT contrast properties and excretion of biocompatible sub-5 nm nanoparticles will be investigated via CT imaging of wild type mice. The mice will be anesthetized via an intramuscular injection of ketamine (100 mg/kg) and xylazine (10 mg/kg). The mice will be prescanned using a preclinical CT (ImTek, Knoxville, Tenn.), operating at 0.1 mm resolution and 80 kV. CT images of mice injected with a 2 nm, glucose coated gold nanoparticles are displayed in FIG. 15. As can be seen, this formulation accumulates in the kidneys and bladder at 5 min post-injection and has primarily accumulated in the bladder at 120 min post-injection, indicating swift kidney excretion. The lead formulations will be injected into wild type mice (n=3 per group) at a dose of 500 mg Au/kg and their excretion followed by imaging the mice over the succeeding two hours (i.e. at 5 min, 30 min, 1 hr and 2 hr). Images will be analyzed using Osirix 64 bit (v3.7.1). Excretion via the kidneys and urine is expected to be observed by the appearance of hyperintensities (i.e. an increase of >100 Hounsfield Units) in the kidneys and bladder.

The mice for whom swift nanoparticle excretion is observed will be sacrificed using $CO_2$ at 24 hours post-injection, perfused with PBS and dissected. Biodistribution will be done using inductively coupled plasma optical emission spectroscopy (ICP-OES) performed on a Spectro Genesis ICP. Formulations for whom <5% retention was observed at this timepoint will be further studied for its excretion characteristics in a mouse model of chronic kidney dysfunction (CKD) to confirm excretion even in the presence of kidney disease. CKD will be induced in male BALB/c mice by administration of a single dose of Adriamycin (10.4 mg/kg) via the tail vein injection of non-anesthetized mice. After 3 weeks, Adriamycin-induced nephropathy in CKD mice will be confirmed by serum creatinine measurement. At this time point, the best-excreted formulations from WT experiments (up to ten formulations) will be trialed in these mice (n=3). Iopamidol and larger gold nanoparticles (15 nm), with the same coatings as the small nanoparticles, will be used as positive and negative controls, respectively.

Assuming excretion is observed in CKD mice also, these formulations will be injected into further groups of mice. Blood draws will be taken from these mice over four hours and will be analyzed with ICP-OES to determine the blood half-life (the expected half-life is around 30 minutes, so four hours is an appropriate length of time to gather data). At the end of this timeframe, whole blood will be obtained by cardiac puncture and stored in EDTA coated tubes. The samples will be centrifuged at 8000 g for 30 min and the serum collected. The serum will subjected to a biochemistry panel (ALX laboratories, NY) analysis to determine the blood concentrations of alanine transaminase, aspartate transaminase, creatinine and creatine kinase, circulating markers for tissue damage (in particular, creatinine is a marker for kidney damage).

These animals will then be perfused with PBS and their organs dissected. Tissue will be prepared for histological investigation by embedding in Optimal Cutting Temperature media, frozen, sectioned, fixed in 4% paraformaldehyde and stained with hematoxylin and eosin. Hematoxylin and eosin stained slides of the organs of gold nanoparticle injected mice will be imaged and inspected for signs of toxicity (necrosis or cell death). Organs from control animals used for comparison. If necrosis is observed, the extent will be recorded as a percentage of the total tissue area on the slide.

Small pieces (1 mm$^3$) of organs will be prepared for TEM imaging via fixation in glutaraldehyde, followed by osmium tetraoxide and stained post-sectioning with 4% uranyl acetate and Reynold's lead citrate. The organs will be examined for any retention of gold nanoparticles and their location.

Expected results: we expect that biocompatible gold nanoparticles of <5 nm that can be excreted >95% within 24 hours can be found. We expect that in vivo markers of tissue damage will be no different from control.

Alternatives and pitfalls: If the nanoparticles are not sufficiently excreted, the coating characteristics of the best excreted formulations will be examined and new formulations will be generated with different combinations of the best ligands and also with new ligands that have similar chemical structures. Additionally, smaller nanoparticles with the same coatings will be trialed.

Encapsulation of Gold Nanoparticles Into Polyphosphazene Polymer

Small gold nanoparticles will be encapsulated into slow-releasing polyphosphazene polymer and evaluate them as CT contrast agents and for excretion.

Methods will be developed to encapsulate excretable and biocompatible gold nanoparticles into polymer nanoparticles in high yield. The resulting nanoparticles will be studied for their biocompatibility and degradation rates. The most biocompatible formulations will be evaluated in vivo for the CT contrast produced and excretion. Such polymer-gold core nanoparticles will be advantageous, as larger nanoparticles can give long-lasting vascular contrast and their slow degradation over time should result in low concentrations of contrast agent at the kidney at any time, reducing the chance of adverse effects.

Gold Core Encapsulation in Polymer Nanoparticles

The three best excreted/most biocompatible gold nanoparticles identified above will be explored for their ability to be encapsulated in biodegradable polyphosphazene matrices. Initially poly-di(carboxylatophenoxy)phosphazene (PCPP) will be used. This polyphosphazene has been shown to degrade over time in aqueous media, via hydrolysis of the polymer backbone. Furthermore, particles can be made from this polymer that incorporate proteins with up to 94% inclusion efficiency. Such encapsulated proteins are released over time, at rates that depend on the protein in question. The gold nanoparticles will be entrapped in the nanospheres via hydrogen bonding and ionic, acid-base attractions. This hydrophilic polymer nanoparticle represents a novel platform for the development of contrast agents.

Figure 16A:
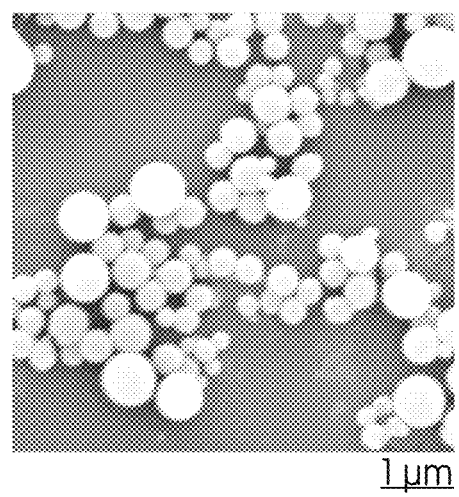
FIG. 16 shows (a) electron microscopy images of PCPP nanoparticles and (b) gold glutathione-loaded PCPP nanoparticles, and (C) a CT image of gold-PCPP nanoparticles.
Figure 16B:
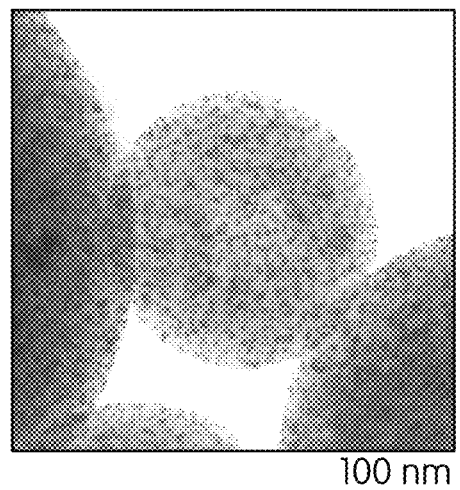
Figure 16C:
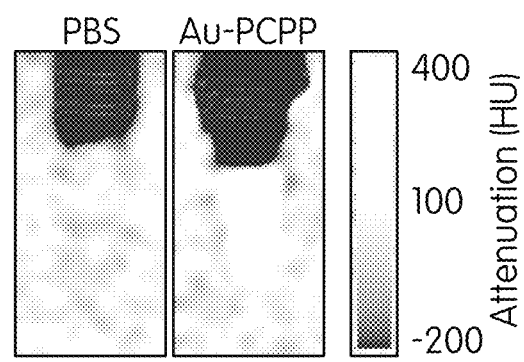

Polyphosphazene nanoparticles (PCPP-NP) loaded with gold nanoparticles have been created. An SEM image of PCPP-NP is shown in FIG. 16A. Glutathione, 11-mercaptoundecanoic acid and citrate coated gold nanoparticles were encapsulated in these hydrophilic polymer-based nanoparticles. For example, a TEM image of PCPP-NP loaded with 5 nm glutathione coated gold nanoparticles (as discussed above) is shown in FIG. 16B. A general method for the synthesis of PCPP-NP is as follows. PCPP will be dissolved in an aqueous solvent at a concentration of 0.5% and the pH adjusted to 7.4. Stock solutions of spermine will be made in the same solvent (pH 7.4) at a concentration of 7%. 1 ml of PCPP solution, diluted to the desired concentration, will be mixed with the loading material. For example, 0.1 ml of glutathione coated gold nanoparticles (10 mg Au/ml, deionized water) was added to 1 ml of 0.2% PCPP to create the nanoparticles seen in FIG. 16B. Spermine will then be added to create the desired final concentration (e.g. 0.097%) and the solution mixed. A suspension forms upon mixing. This suspension will be immediately added to 100 ml of 8.8% $CaCl_2$ solution. After stirring for 30 minutes, the resulting nanoparticles are isolated by centrifugation and washed with deionized water, which will remove any non-entrapped gold nanoparticles. In preliminary experiments with 15 nm gold nanoparticles, it has been found that PCPP-NP can be formed and entrapped within them varying loads of gold nanoparticles, up to a 10:1 gold:polymer mass ratio. These formulations can produce strong CT contrast, as seen in FIG. 16C, where a 17.2 mg Au/ml solution is shown. These nanoparticles were found to be taken up by J774A.1 macrophage cells, when incubated at 0.5 mg Au/ml for 24 hrs. This result indicates the need for passivation of the nanoparticle surface to avoid uptake by the reticuloendothelial system.

The PCPP-NP will be coated with polyethylene glycol (PEG) to provide long circulation half-lives and avoid uptake by the reticuloendothelial system. The three possibilities are to chemically modify the polymer, chemically modify the spermine or to add PEG molecules that terminate in acids or amines (FIG. 1). The polymer could be coupled with small amounts of amines such as methylamine or an amino-PEG molecule. Small proportions of the spermine could be modified with acids such as a carboxy-PEG. Last, amino-PEG or carboxy-PEG could be added at various points in the reaction process. The size will be controlled via the concentration of the polymer and by varying the amount of PEG included in the synthetic process. By these means nanoparticles will be produced of approximately 100 nm in diameter. These nanospheres could be modified with fluorophores, drugs, targeting moieties and other desired features.

The gold loaded polyphosphazene nanospheres will be characterized with scanning electron microscopy (SEM, FEI 600 Quanta FEG), TEM (FEI Tecnai T12) and DLS (Zetasizer Nano ZS90). Nanocrystal distribution will be examined with electron tomography using a FEI Tecnai T12. The gold concentration will be probed by dispersing the nanospheres in 1 ml of buffer, scanning them with CT and comparing the image intensities with a standard curve (CT attenuation is linear with gold concentration). ICP-OES will be used to confirm the results found from CT for the formulations with highest gold inclusion.

Expected results: We expect that PCPP-NP with gold loading of >10 mg Au/mg polymer will be possible (the density of gold is 19.3 g/cm$^3$, so such high loadings are feasible). High loadings are desirable so that the high concentration solutions needed for X-ray contrast agents can be produced.

Alternatives and pitfalls: should high gold loading not be realized, alternative polyphosphazenes will be explored, such as polyphosphazenes that contain amino acids such as lysine or glutamic acid. Such polymers are commercially available from Sigma Aldrich or CM-Tec (Newark, Del.).

PCPP-NP Biocompatibility and Degradation

Figure 17A:
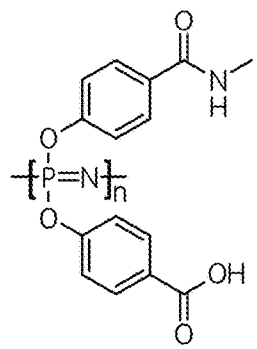
FIG. 17 shows a schematic representation of the formation and degradation of gold nanoparticle-containing nanoclusters.

PCPP-NP will be tested for their stability in biological media by incubating with 10% serum for 1 hour and measuring their size with DLS—an increase in size will indicate a lack of stability (a decrease in size may be observed due to degradation). Toxicity and physiochemical parameters of the as synthesized nanoparticles will be screened using the same techniques as outlined above. Data shows gold loaded PCPP-NP to be biocompatible even after incubation for 24 hours at 0.5 mg Au/ml (FIG. 17A). Additional toxicity screening will be done on PCPP-NP samples that are aged for one week in cell culture media, to test the toxicity of the breakdown products.

Figure 17B:
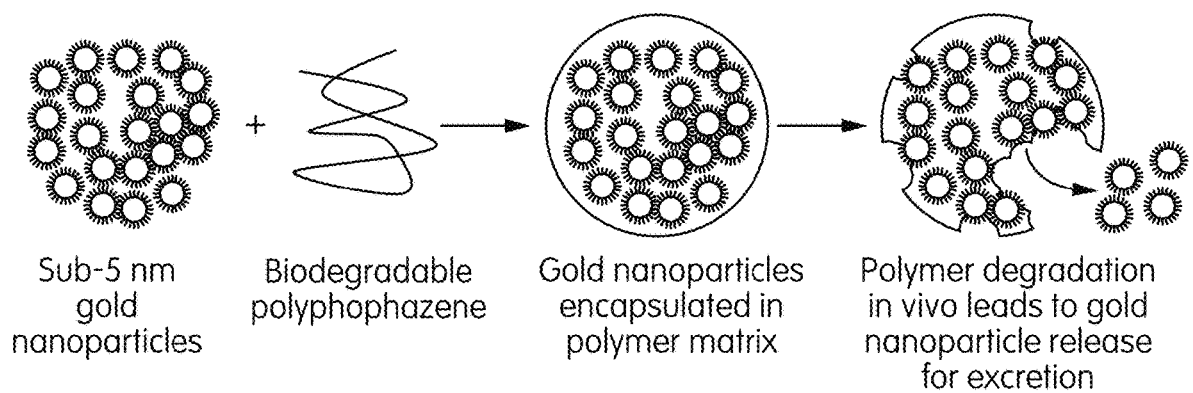

The PCPP-NP with highest gold inclusion for each formulation will be tested for gold nanoparticle release, by placing a sample (1 ml) in a dialysis membrane (100 kD MWCO—this should not allow the PCPP-NP to pass, but the small gold nanoparticles should—this will be tested and an alternative MWCO membrane used if need be). The membrane will be placed in 1 l of HEPES buffered saline containing 10% serum at 37° C. The gold content of the sample inside the membrane will be sampled after 1, 2, 4, 8, 24, 48, 72, 96 and 168 hours of incubation and analyzed via ICP-OES. Data demonstrating the degradability of gold loaded PCPP-NP is displayed in FIG. 17B-D. The nanoparticles are stable in PBS at pH 7.4 (the pH of blood), whereas at pH 6 (the pH of endosomes), the nanoparticles dissociated, as evidenced by the red color of free gold nanoparticles in solution (FIG. 17B). TEM on cells incubated with PCPP-NP revealed that the aggregates break down in vitro, as dispersed gold cores were observed within cells (FIG. 17C). When 100% confluent macrophages were incubated with PCPP-NP for 24 hours, then incubated with fresh media, we observed a reduction in the gold content in the cells over time, indicating that the PCPP-NP were being degraded and the gold released (FIG. 17D). Last, we evaluated gold core release via incubating Au-PCPP in 10% serum in PBS at 37° C. for 7 days and sampling the liquid periodically. The samples were centrifuged to exclude Au-PCPP and the released gold cores in the supernatant evaluated with ICP-MS (FIG. 17E). We observed 59% release within 7 days, providing strong evidence for the biodegradability of Au-PCPP.

Expected results: We expect that we will be able to identify PCPP-NP formulations that are stable WRT aggregation, have low toxicity and break down within a week.

Alternatives and pitfalls: Should gold release be too fast, polyphosphazenes with higher molecular weight or alternative cross-linkers will be explored. Alternatively, the PCPP-NP could be coated with more or longer PEG chains, such as PEG 5000. If degradation is too slow, the PEG coating could be reduced, or the molecular weight of the polymer. Addition of more/longer PEG could also be used to address issues of stability or toxicity. An alternative method to control bioerosion of the phosphazene polymer is to utilize different ratios of amino acid ester side groups, which are known to accelerate erosion in aqueous media.

PCPP-NP CT Contrast and In Vivo Biocompatibility

The optimal PCPP-NP identified above for each of the three best-excreted gold nanoparticle formulations will be tested for CT contrast properties, biocompatibility and gold excretion in mice in vivo. Although the gold nanoparticle release will have been carefully tested in vitro, in vivo conditions may result in different rates of release. PCPP-NP will be injected into mice at a dose of 250 mg Au/kg via the tail vein. Eight mice per group will be used. The mice will be scanned using a similar imaging protocol to that mentioned above. However, as opposed to the experiments above, it is expected that prolonged contrast will be observed in the vasculature, with contrast observed for several hours, therefore these mice will be scanned at 5 min, 1 hr, 2 hrs, 6 hrs and 24 hrs post-injection.

After imaging, mice will be placed in metabolic cages, which allow their feces and urine to pass through the cage floor. The feces and urine will be collected on days 1, 3, 5, 8, 11, 15, 20, 25 and 30 post-injection. Gold content in urine and feces will be separately analyzed with ICP-OES. At day 30 the mice will be sacrificed using $CO_2$, perfused with PBS and their heart, lungs, liver, kidneys and spleen harvested. These organs and the carcass will be analyzed with ICP-OES for gold retention. Additional groups of mice will be injected with PCPP-NP containing 15 nm core gold nanoparticles with the same coatings as the small gold nanoparticles, as a control. The comparative excretion time and biodistribution of these particles will be explored, as well as compare the results obtained with those from iopamidol obtained under the experiments above.

Additional groups of WT and CKD mice (n=6 per group) will be injected with PCPP-NP, and small amount of their blood drawn at various timepoints up to 24 hours to determine the blood circulation half-life of the agents (ICP-OES analysis for gold). At 24 hours, their blood will be drawn by cardiac puncture. The blood will be analyzed as per above for circulating markers of tissue damage. The mice will be perfused and their organs will be dissected. The organs will be prepared for histological analysis as described above. Control CKD and WT mice will receive saline.

Expected results: 99% of the gold dose will be excreted by 30 days. The majority of the dose will be excreted via the urine. No difference in serum or histological markers of tissue damages in each mouse type compared to control will be observed.

Alternatives and pitfalls: If the gold excretion is too slow in vivo, PCPP-NP formulations will be generated with lower molecular weight polyphosphazenes or greater amino acid content. If the gold excretion is too fast, the opposite strategies will be undertaken or the density/molecular weight of PEG coating will be increased.

We claim:

1. A nanocluster comprising:
    a plurality of hydrophilic inorganic nanocrystals, each comprising:
        a gold nanocrystal having a mean size of about 5 nm or less; and
        a first hydrophilic ligand coating selected from the group consisting of: 11-mercaptoundecanoic acid, glutathione and citrate;
    a hydrophilic biodegradable polymer encapsulating the plurality of hydrophilic inorganic nanocrystals, wherein:
        the hydrophilic biodegradable polymer is adapted to degrade over time by hydrolysis; and
        the hydrophilic biodegradable polymer is polyphosphazene; and
    a second ligand coating the surface of the hydrophilic biodegradable polymer, wherein the second ligand is PEG;
    wherein the nanocluster has a mean size in the range of from about 10 nm to about 300 nm.

2. The nanocluster according to claim 1, wherein the polyphosphazene is selected from the group consisting of poly(bis(4-carboxyphenoxy)phosphazene) (PCPP) and poly (carboxylatophenoxy)(glycinato) polyphosphazenes (PCGPPs).

3. The nanocluster according to claim 1, wherein the polymer is crosslinked.

4. The nanocluster according to claim 3, wherein the polymer is crosslinked with spermine.

5. The nanocluster according to claim 1, wherein the plurality of hydrophilic inorganic nanocrystals are positioned on a surface of the polymer.

6. The nanocluster according to claim 1, further comprising a drug contained on the surface of the nanocluster, contained within the core of the nanocluster, dispersed throughout the nanocluster, or a combination thereof.

7. A method comprising:
  administering to a patient a plurality of nanoclusters according to claim 1; and
  imaging the patient with x-ray imaging, computed tomography (CT), magnetic resonance imaging (MRI), photoacoustic imaging, fluorescence, or fluoroscopy.

8. A method for enhancing the effect of radiation therapy, comprising:
  administering to a patient a plurality of nanoclusters according to claim 1; and
  treating the patient with radiation at a targeted site, wherein the plurality of nanoclusters increase the amount of radiation absorbed at the targeted site.

9. A method for ablating tissue, comprising:
  administering to a patient a plurality of nanoclusters according to claim 1; and
  treating the patient with electromagnetic radiation at a targeted site, wherein the plurality of nanoclusters absorb the electromagnetic radiation and convert the electromagnetic radiation to heat to ablate the tissue at the targeted site.

* * * * *